United States Patent
Wang et al.

[11] Patent Number: 5,942,103
[45] Date of Patent: Aug. 24, 1999

[54] RENEWABLE-REAGENT ELECTROCHEMICAL SENSOR

[75] Inventors: Joseph Wang, Las Cruces, N.Mex.; Khris B. Olsen, Richland, Wash.

[73] Assignee: New Mexico State University Technology Transfer Corporation, Las Cruces, N.Mex.

[21] Appl. No.: 08/915,284

[22] Filed: Aug. 20, 1997

Related U.S. Application Data

[63] Continuation-in-part of application No. 08/383,717, Feb. 3, 1995, Pat. No. 5,676,820.

[51] Int. Cl.⁶ .................................................. G01N 27/26
[52] U.S. Cl. .................. 205/787; 205/777.5; 205/778; 205/789.5; 205/790; 205/792; 205/793; 204/409; 204/412; 204/415; 204/434
[58] Field of Search .................................. 204/409, 412, 204/415, 434; 205/777.5, 778, 787, 789.5, 790, 792, 793

[56] References Cited

U.S. PATENT DOCUMENTS

| | | |
|---|---|---|
| 1,707,291 | 4/1929 | Waite et al. . |
| 3,094,692 | 6/1963 | Westneat, Jr. et al. . |
| 3,259,568 | 7/1966 | Jordan et al. . |
| 3,410,793 | 11/1968 | Stranahan et al. . |
| 3,855,099 | 12/1974 | Matson . |
| 3,904,487 | 9/1975 | Lieberman et al. . |
| 3,943,488 | 3/1976 | Kazahaya . |
| 3,948,681 | 4/1976 | Barger, Jr. et al. . |
| 4,003,705 | 1/1977 | Buzza et al. . |
| 4,058,446 | 11/1977 | Zirino et al. . |
| 4,077,030 | 2/1978 | Helava . |
| 4,090,926 | 5/1978 | Matson . |
| 4,172,770 | 10/1979 | Semersky et al. .................. 204/1 T |
| 4,201,646 | 5/1980 | Matson . |
| 4,327,166 | 4/1982 | Leger . |
| 4,374,041 | 2/1983 | Matson . |
| 4,524,354 | 6/1985 | Morgan . |

(List continued on next page.)

FOREIGN PATENT DOCUMENTS

| | | |
|---|---|---|
| 0 569 908 A2 | 11/1993 | European Pat. Off. . |
| 1 505 553 | 3/1978 | United Kingdom . |
| WO89/09388 | 10/1989 | WIPO . |
| WO91/08474 | 6/1991 | WIPO . |
| WO92/18857 | 10/1992 | WIPO . |

OTHER PUBLICATIONS

Hilton, J., et al., "Monitoring in the Vadose Zone at Two Inactive Uranium Mill Tailings Sites," *Geotechnical and Geohydrological Aspects of Waste Management Symp.*, pp. 439–446, Abstract Only (Feb. 5, 1986).

Hinton, E.R., Jr., et al., "Development of an On–Line Mercury Stream Monitor," *Environ. Sci. Technol.*, vol. 21, No. 2, pp. 198–202, Abstract Only (Feb. 1987).

Hopkins, W.C., "Three Mile Island Unit 2: The Early Radiological Conditions of the Reactor Building," *Joint Meeting of European Nuclear Soc. and Amer. Nuclear Soc., Trans. Am. Nucl. Soc.*, vol. 57, pp. 447–449, Abstract Only (Oct. 30 –Nov. 4, 1988).

(List continued on next page.)

*Primary Examiner*—T. Tung
*Assistant Examiner*—Jennifer McNeil
*Attorney, Agent, or Firm*—Rod D. Baker; Deborah A. Peacock

[57] ABSTRACT

A new electrochemical probe(s) design allowing for continuous (renewable) reagent delivery. The probe comprises an integrated membrane-sampling/electrochemical sensor that prevents interferences from surface-active materials and greatly extends the linear range. The probe(s) is useful for remote or laboratory-based monitoring in connection with microdialysis sampling and electrochemical measurements of metals and organic compounds that are not readily detected in the absence of reacting with the compound. Also disclosed is a method of using the probe(s).

18 Claims, 11 Drawing Sheets

U.S. PATENT DOCUMENTS

| | | |
|---|---|---|
| 4,545,382 | 10/1985 | Higgins et al. . |
| 4,568,935 | 2/1986 | Phillips et al. . |
| 4,586,136 | 4/1986 | Lewis . |
| 4,601,886 | 7/1986 | Hudgins . |
| 4,622,276 | 11/1986 | Walsh . |
| 4,626,992 | 12/1986 | Greaves et al. . |
| 4,628,315 | 12/1986 | Douglas . |
| 4,661,210 | 4/1987 | Tenygl . |
| 4,695,555 | 9/1987 | O'Keeffe . |
| 4,783,748 | 11/1988 | Swarztrauber et al. . |
| 4,786,373 | 11/1988 | Saloheimo et al. . |
| 4,804,443 | 2/1989 | Newman et al. . |
| 4,831,558 | 5/1989 | Shoup et al. . |
| 4,844,887 | 7/1989 | Galle et al. . |
| 4,865,992 | 9/1989 | Hach et al. . |
| 4,888,295 | 12/1989 | Zaromb et al. . |
| 4,960,711 | 10/1990 | Aoki et al. . |
| 5,019,515 | 5/1991 | Gisin et al. . |
| 5,045,214 | 9/1991 | Walker . |
| 5,091,299 | 2/1992 | Turner et al. . |
| 5,120,421 | 6/1992 | Glass et al. . |
| 5,131,999 | 7/1992 | Gunasingham . |
| 5,176,881 | 1/1993 | Sepaniak et al. . |
| 5,191,327 | 3/1993 | Talmadqe et al. . |
| 5,192,416 | 3/1993 | Wang et al. . |
| 5,237,031 | 8/1993 | Kubota et al. . |
| 5,254,235 | 10/1993 | Wu . |
| 5,292,423 | 3/1994 | Wang . |
| 5,296,125 | 3/1994 | Glass et al. . |
| 5,298,129 | 3/1994 | Eliash ................................ 204/153.1 |
| 5,333,114 | 7/1994 | Warrior et al. . |
| 5,366,634 | 11/1994 | Vijayan et al. . |
| 5,389,215 | 2/1995 | Horiuchi et al. . |
| 5,422,014 | 6/1995 | Allen et al. . |
| 5,434,084 | 7/1995 | Burgess, Jr. . |
| 5,437,772 | 8/1995 | De Castro et al. . |
| 5,462,645 | 10/1995 | Albery et al. ...................... 204/153.12 |
| 5,512,489 | 4/1996 | Girault et al. . |
| 5,554,268 | 9/1996 | Priddy et al. . |
| 5,635,054 | 6/1997 | Girault et al. . |
| 5,676,820 | 10/1997 | Wang et al. . |

OTHER PUBLICATIONS

Huiliang, H., et al., "Carbon Filter Electrodes in Flow Potentiometric Stripping Analysis," *Analytical Chimica Acta,* vol. 193, pp. 61–69 (1987) Month Unavailable.

Indig, M.E., "In Situ Electrochemical Measurements in BWRs," Proc.: 1989 Workshop on LWR Radiation Water Chemistry and its Influence on In–Core Structural Materials, Abstract Only (Nov. 14–15, 1989).

Instrument Soc of America, "International European Region Conference on Environmental Protection, Control and Monitoring," Instrument Soc. of America, 104 p, Abstract Only (May 22–24, 1991).

Janata, J., "Potentiometric Gas Sensors Based on Field Effect Transistors," Pittsburgh Conf. and Exp. on Analytical Chem and Applied Spec., Abstract Only (Mar. 1987).

Journal of Animal Production Research, "Physiological Variations in Snails Bulinus–Phyopsis–Globosus inthe Laboratory and Parts of Oyo State, Nigeria," *Journ. of Animal Production Research,* vol. 9, No. 1–2, pp. 43–52, Abstract Only (Sep. 1989).

Keeny, W.L., et al., "Determination of Trace Metals in Cladophora Glomerata: C Glomerata as a Potential Biological Monitor," *Water Res.,* vol. 10, No. 11, pp. 981–984, Abstract Only (1976) Month Unavailable.

Klainer, S., et al., "Monitor for Detedting Muclear Waste Leakage in a Subsurface Repository," Lawrence Berkeley Lab CA USA, Abstract Only (Nov. 5, 1980).

Klatt, L.N., et al., Fiber Optic Sensors for the Study of Falling Liquid Films, Symp. on Chem. Sensors and Microinstrumentation, 120 p, Abstract Only (Sep. 25–30, 1988).

Kovalevskii, A.L., et al., Determination of Zinc in Tree Crust by Field X–Ray Analyzers, *Kokl, Akad, Nauk SSR (USSR),* vol. 251, No. 1, pp. 173–175, Abstract Only (1980) Month Unavailable.

Kramar, U.J., et al., "Application of Energy Dispersive X–Ray Fluorescence, Ion Sensitive Electrodes and Instrumental Neuron Activation in Geochemical Prospecting," Bundes–ministerium fuer Forshung und Technologie, Bonn (Germany), Abstract Only (1982) Month Unavailable.

Kubiak, W.W., "Anotic–Stripping Voltammetry of Heavy Metals in the Presence of Organic Surfactants," *Talanta,* vol. 36, No. 8, pp. 821–824 (Feb. 1989).

Kueppers, G., "Development of Activation Analytical Methods for the Determination of Trace Amounts in Natural Wastes," Technische Hochschule Aachen (Germany, F.R.), Abstract Only (Jan. 27, 1981).

Leonard, P.H., "Implementation of a Field Portable X–Ray Fluorescence System at the C C Batters Superfund Site," *Proc. of Nat'l Research and Dev. Conf. on Control of Hazardous Materials,* 549 p, pp. 523–525, Abstract Only (Feb. 20–23, 1991).

Lerch, K., "Neuorspora Tyrosinase: Structural, Spectroscopic and Catalytic Properties," *Molecular and Cellular Biochemistry,* vol. 42, pp. 125–138 (1983) Month Unavailable.

Levine, H.G., Greef Seaweed Ulva as Monitor for Pollution in Coastal Waters, Univ. of MA Thesis, Abstract Only (1983) Month Unavailable.

Lieberman, S.H., et al., Fluorescence–Based Fiber Optic Chemical Sensors for Direct Determination of Trace–Transitio Metals in Seawater, Amer. Geophysical Union 1988 Fall Meeting, Abstract Only (Fall, 1988).

MacCarthy, P., et al., "Water Analysis," *Anal. Chem.,* vol. 65, pp.244R–292R (Jun. 1993).

McLaughlin, K., et al., "Anodic Stripping Voltammetry of Selenium (IV) at a GoldFiber Working Electrode," *Electroanalysis,* vol. 4, pp. 689–693 (1992) Month Unavailable.

Malito, M.L., "Ancillary Operations in Coal Preparation Instrumentation On–Line Low Cost Sulfur and Ash Analyzer," Babcock and Wilcox Co., 343 p, Abstract Only (Jul. 1991).

Manushev, B., et al., "In–Situ Gamma Spectroscopic Measurement of Natural Waters in Bulgaria," *Bulg. J. Phys.,* vol. 10, No. 4, pp. 441–415, Abstract Only (1983) Month Unavailable.

Mednikov, E.P., et al., "Remote Sampling of Radioactive Aerosols at Atomic Power Stations," *Sov. At. Energy,* vol. 62, No. 1, pp. 49–62, Abstract only (Jul. 1987).

Meyers–Schoene, L., "Comparison of Two Freshwater Turtle Species as Monitors of Environmental Contamination," Univ. of Tenn. Thesis, 163 p, Abstract Only (Apr. 1990).

Micheletti, W.C., et al., "Cooling Water Treatment Field Testing for Scaling Control," *Electric Power Research Int.,* Proc. of Amer. Power Conf., vol. 46, pp. 954–959, Abstract Only (Apr. 24, 1984).

Munkata, T., et al., "Fuzzy Systems: An Overview," *Communications of the ACM,* vol. 37, No. 3, pp. 69–84 (Mar. 1994).

Murphy, E.M., et al., "Evaluation of Chemical Sensors for In–Situ Ground–Water Monitoring at the Hanford Site," *Pacific Northwest Lab, Richland, WA USA,* Report PNL–6854, p. 85, Abstract Only (Mar. 1989).

Nielsen, H.O., "Environment and Pollution Measurement Sensors and Systems," *SPIE,* 207 p, Abstract Only (Mar. 12–16, 1990).

Oak Ridge National Lab TN USA, "Industrial Safety and Applied Health Physics, Annual Report," 133 p, Abstract Only (Nov. 1981).

Olsen, K.B., et al., "On–Site Analysis of Metals in Soils Using Stripping Voltammetry," *Conference: Information Exchange Meeting on Characterization Sensors,* p. 3, paper 30 (261 p) Abstract Only (Jul. 1992).

Ortega, F., et al., "Liquid Chromatographic Separation of Phenolic Drugs Using Catalytic Detection: Comparison of an Enzyme Reactor and Enzyme Electrode," *J. of Pharm. & Biomed. Analysis,* vol. 10, Nos. 10–12, pp. 789–796 (1992) Month Unavailable.

Ortiz, A., "Advance in the Research and Use of Remote Sensors in Natural Resources Development Studies: Chile," *12th Int'l Symp. on Remote Sensing of Environment,* vol. 1 pp. 1583–1585, Abstract Only (1978) Month Unavailable.

Ostapczuk, P., "Present Potentials and Limitations in the Determination of Trace Elements by Potentiometric Stripping Analysis," *Analytica Chimica Acta,* pp. 35–40 (1993) Month Unavailable.

Pacific Nortwest Lab, "Ground Water Monitoring Compliance Projects for Hanford Site Facilties," Abstract Only (Nov. 1987).

Packer, T.W., "Determination of the Concentration of Uranium in Soil and Stream Sediment Samples Using a High Resolution Energy–Dispersive X–Ray Fluorescence Analyzer," *Int. J. Appl. Radiat. Isotopes,* vol. 34, No. 1, pp. 273–281, Abstract Only (Jan. 1983).

Perone, S.P., et al., "Application of Mercury–Plated Graphite Electrodes to Voltammetry and Chronopotentiometry," *J. Electroanal. Chem.,* vol. 12, pp. 269–276 (1966) Month Unavailable .

Perrin, M., "Plant Analyzers and Part Task Simulators," *Proc.: 1988 Conf. on Power Plant Simulators and Modeling,* 716 p, Abstract Only (Jun. 15–17, 1988 and Feb. 1990).

Phillips, D.J.H., "Use of Biological Indicator Organisms to Monitor Trace Metal Pollution in Marine and Estuarine Environments: A Review," *Environ Pollut.,* vol. 14, No. 4, pp. 281–317 Abstract Only (Aug. 1977).

Piorek, S., et al., "A New Calibration Technique for X–Ray Analyzers Used in Hazardous Waste Screening," *Hazardous Waste and Hazardous Materials Conference,* pp. 428–433, Abstract Only (Apr. 19–21, 1988).

Radwanowski, L.J., "Equipment for Measuring Radiation," *Tech. Poszukiwan Geol. (Poland),* pp. 428–433, Abstract Only (1979) Month Unavailable.

Ray, S.N., et al., equisetum Arvense—an Aquatic Vascular Plant as a Biological Monitor for Heavy Metal Pollution, *Chemophere (UK),* vol. 8, No. 3, pp. 125–128 (1979) Month Unavailable.

Rasmussen, L., et al., "Soil Water Samplers in Ion Balance Studies on Acidic Forest Soils," *Bull. Environ. Contam. Toxicol.,* vol. 36, No. 4, pp. 563–570, Abstract Only (Apr. 1986).

Rivas, G., et al., Electrochemical Determination of the Kinetic Parameters of Mushroom Tyrosinase, *Bioelectrochemistry and Bioenergetics,* vol. 29, pp. 19–28, Abstract (1992) Month Unavailable.

Robertiello, A., et al., Nickel and Vanadium as Biodegradation Monitors of Oil Pollutants in Aquatic Environments, *Water Res. (UK),* vol. 17, No. 15, pp. 497–500 Abstract Only (1983) Month Unavailable.

Schiager, K.J., et al., Simple Field Method for Determining Compliance with EPA Land Cleanup Standards, *Ann. Symp. on Uranium Mill Tailings Management,* pp. 135–148, Abstract Only (Dec. 9, 1982).

Semonin, R.G., Study of Air Pollution Scavenging, 14th Progress Report, Illinois State Water Survey, Abstract Only (Apr. 1976).

Sevastianov, O.N., "Using Strontium to Monitor the Flooding of Oil Wells in the Orenburg Field," *Geol. Nefti Gaza (USSR),* pp. 32–34, Abstract Only (1980) Month Unavailable.

Sharma, S.K., "Study of Corrosion of Metals in the Marine Environment Using Raman Spectroscopy and Development of Fiber Optics Sensors for In Situ Monitoring of Corrosion Parameters," Hawaii Natural Energy Insti., Univeristy of Hawaii, Abstract Only (1987) Month Unavailable.

Shyong, J., et al., "Analysis of Uranium, Thorium, and Potassium in the Soil and Rocks in Northwester Taiwan," *Computer Appl. in Health Physics,* pp. 7141–7145 Abstract (1984) Month Unavailable.

Simpson, W.R., et al., "In–Situ Deep Water Particle Sampler and Real–Time Sensor Package with Data from the Madeira Abyssal Plain," *Inst. Oceanogr. Sci.,* vol. 34, No. 8, pp. 1477–1498, Abstract Only (1987) Month Unavailable.

Singh, U.P., et al., "Sampling the Biscayne Aquifer for Toxic Pollutants," *Conf. on Manage–ment of Municipal, Hazardous and Coal Wastes,* pp. 422–431, Abstract Only (Sep. 1984).

Smith, W.J., et al., "In Situ Gross Alpha Monitoring Technique for Delineating Fugitive Mill Tailings," Int'l Symp. on Mgmt. of Waste From Uranium Mining and Milling, pp. 621–632, Abstract Only (May 1982).

Smyrniotis, C.R., "Mobile Monitoring and Process Simulation for High Heat Flux Cooling Water Systems," *Proc. of Instr. and Control Systems Conf. and Exhibit,* pp. 133–134 Abstract Only (Mar. 1987).

Spencer, C.M., "Progress and Performance of On–Line Analyzers of Coal," *Symp. on Instr. and Control for Fossil Energy Processes,* pp. 619–633, Abstract Only (Jun. 7, 1982/Sep. 1982).

Stewart, K.K., "Flow Injection Analysis," *Analytical Chem.,* vol. 55, No. 9, pp. 931A, 1040A from No. 11 and attachments Abstract Only (Aug. and Sep. 1983, resp.).

Stolzenburg, T.R., et al., "Preliminary Results on Chemical Changes in Groundwater Samples Due to Sampling Devices," Residuals Management Technology, Inc., Madison, WI, 110, Abstract Only (Jun. 1985).

Stuart, T.P., "Limiting Values for Radionuclide Concentration in the Soil from Remote Spectrometer Measurements," EG & G, Inc., Las Vegas NV, 38 Abstract Only (Aug. 1977).

Symader, W., et al., "The Dynamics of the Conveyance of Suspended Particles and Its Relevance to Water Quality Proglems," *Annual Meeting, Fachgruppe Wasserchemie of Gesselchaft Deutscher Chemiker,* pp. 159–169, Abstract Only (Dec. 1991).

Takeda, Y., "Development of Ultrasound Velocity Profile Monitor and its Experience," *4th Int'l Topical Meeting on Nuclear Reactor Thermal–Hydraulics,* pp. 418–423, Abstract Only (Oct. 10–13, 1989).

Takeuchi, M., et al., "Geophysical Monitoring System of Diffusing Electrolyte Injected into Groundwater," *Nat'l Res. Inst. of Agri. Eng. (Japan)*, pp. 12–18, Abstract (Mar. 25, 1990).

Talmage, S.S., "Comparative Evaluation of Several Small Mammal Species as Monitors of Heavy Metals, Radionuclides and Selected Organic Compounds in the Environment," Univ. of Tenn Thesis, 193p, Abstract Only (1989).

Tarlov, M.J., et al., "PH Sensors Based on Iridium Oxide," Eng. Nat'l Inst. of Standards and Tech., 20 pp, Abstract Only (Mar. 1990).

Tercier, M.L., "In Situ Voltammetric Measurements in Natural Waters: Future Prospects and Challenges," *Electroanalysis*, vol. 5, pp. 187–200 (1993).

Toenniben, A., et al., "Applicaiton of a CW Chemical Laser for Remote Pollution Monitoring and Process Control," *Appl. Phys.*, vol. 18, pp. 297–304 Abstract Only (1979).

Vaughan, B.E., "Multitechnology and Supporting Research Programs," *Battele Pacific Northwest Labs*, pp. 7.1–7.31, Abstract Only (Feb. 1978).

Viswambaran, K.R., et al., "Assessment of Background Radiation Levels at Madras Atomic Power Station," *Bulletin of Radiation Protection (India)*, vol. 11, Nos. 3–4, pp. 161–165 Abstract Only (Jul.–Dec. 1988).

Wang, J., *Analytical Electrochemistry*, Textbook Chapter 2.5, "Controlled Potential Techniques –Stripping Analysis", pp. 27 and 44–53 (1994) Month Unavailable.

Wang, J., *Analytical Electrochemsitry*, Textbook Chapter 3.1 "Electrochemical Cells," pp. 69–70 and Chapter 5.1.1 Enzymes–Based Electrodes pp. 134 and 144 (1994) Month Unavailable.

Wang, J., *Stripping Analysis, Principles, Instrumentation and Applications*, Textbook (1985) Month Unavailable.

Wang, J., et al., Anodic Stripping Voltammetry at Ultramicroelectrodes for Metal Speciation Studies in Aqueous Solutions of Low Ionic Strength, *J. Electroanal. Chem.*, vol.246, pp. 297–305 (1988) Month Unavailable.

Wang, J., et al., "Anodic Stripping Voltammetry as an Analytical Tool," *Environ, Sci. Technol.*, vol. 16, No. 2, pp. 104A–107A (1982) Month Unavailable.

Wang, J., "Adsorptive Stripping Voltammetry — A New Electroanalytical Avenue for Trace Analysis," *J. Res. of Nat'l Bureau of Standards*, vol. 93, No. 3, pp. 489–491 (May–Jun. 1988).

Wang, J., et al., "Batch Injection Analysis," *Analytical Chemistry*, vol. 63, pp. 1053–1065 (May 1991).

Wang, J., et al., "Batch Injection Analysis with Termistor Sensing Devices," *Analytical Letters*, vol. 24, No. 8, pp. 1389–1400 (1991) Month Unavailable.

Wang, J., et al., "Batch Injection with Potentiometric Detection," *Analytical Chimica Acta*, vol. 252, pp. 215–221 (1991) Month Unavailable.

Wang, J., et al., "Mercury–Coated Carbon–Foam Composite Electrodes for Stripping Analysis of Trace Metals," *Analytical Chemistry*, vol. 64, No. 2, pp. 151–155 (Jan. 1992).

Wang, J., et al., "Batch Injection Analysis Using Fiber–Optic Fluorometric Detection," *Applied Spectroscopy*, vol. 46, No. 1, pp. 107–110 (1992) Month Unavailable.

Wang, J., et al., "Gold Ultramicroelectrodes for On–Site Monitoring of Trace Lead," *Electroanalysis*, vol. 5, pp. 809–814, Abstract Only (1993) Month Unavailable.

Wang, J., et al., "Organic–Phase Enzyme Electrode for the Determination of Trace Water in Nonaqueous Media," *Analytical Chemistry*, vol. 65, pp. 845–847 (Mar. 15, 1993).

Wang, J., et al., "Amperometric Biosensor for Phenols Based on a Tyrosinase–Graphite–Epoxy Biocomposite," *Analyst*, vol. 119, (Mar. 1994) Abstract Only.

Wang, J., "Decentralized Electrochemical Monitoring of Trace Metals: From Disposable Strips to Remote Electrodes," *Analyst*, vol. 119, pp. 763–766 (May 1994).

Wang, J., et al., "Stripping Potentiometric Measurements of Copper in Blood Using Gold Microelectrodes," *Analytical Chimica Acta*, vol. 286, pp. 189–195 (1994) Month Unavailable.

Wangsa, J., et al., Fiber–Optic Biosensors Based on the Fluorometric Detection of Reduced Nicotinamide Adenine Dinucleotide, *Anal. Chem.*, vol. 60, pp. 1080–1092 (May 15, 1988).

Wertenbach, H., Determination Methods for Plutonium as Applied in the Field of Reprocessing, *Seminar on Determination Methods for Plutonium as Applied in the Field of Reprocessing*, pp. 77–96, Abstract Only (Oct. 15, 1982/Jul. 1983).

Winklemann, I., et al., "Radionuclide Deposition and Exposure in the Fed. Rep. of Germany after the Chernobyl Accident," Oak Ridge National Lab, TN USA, 30 p, Abstract Only (Nov. 1989).

Wogman, N.A., In–situ X–Ray Fluorescence and Californium–252 Neutron Activation Analysis for Marine and Terrestrial Mineral Exploration, *IAES Int'l Symp. on Nuclear Techniques in Exploration, Extraction and Processing of Mineral Resources*, pp. 447–461, Abstract Only (Mar. 7, 1977).

Wogman, N.A., "Development and Application for an In Situ X–Ray Fluorescence Spectrometer for Underwater Sediment Analysis," *Environ. Int.*, vol. 4, No. 4, pp. 313–324 Abstract Only (1980) Month Unavailable.

Wring, S.A., et al., "Chemically Modified, Screen–Printed Carbon Electrodes," *Analyst*, vol. 117, pp. 1281–1282 (Jan. 7–8, 1992).

Yoneda, K.T., et al., "Characteristics and Correlation of Various Radiation Measuring Methods in Spatial Radiation Measurement," *Ann. Report of Nigata Prefetural Res. Lab for Health and Environ.*, pp. 156–162, Abstract Only (Oct. 1992).

Zauke, G.P., et al., "Biological Indicators of Environmental Quality in the Elbe, Weser and Ems Estaury," Biologie Umweltbudesamt, Berlin (Germany, F.R.), 156 p, Abstract Only (Jul. 1986).

Zirino, A., et al., Measurement of Cu and Zn in San Diego Bay by Automated Anodic Stripping Voltammetry, *American Chem. Soc.*, vol. 12, No. 1, Abstract Only (Jan. 1978).

Gogolak, C.V., et al., "Survey of Gamma Radiation in the Vicinity of theAsse Saltmine Radioactive Wate Disposal Site," Bundesgesundheisamt, Neuherberg (F.R. Germany), Inst. Fuer Strahlenhygiene, Abstract Only (Sep. 1981).

Green, Monika, et al., "Disposable Single–Use Sensors," *Analytical Proceedings*, vol. 28, p. 374, Abstract Only (Nov. 1991).

Grigor'ev, A.I., et al., "Instrumental Neutron–activation Analysis of Oceanic Nodules on a Unit Containing a Radionuclide Neutron Source," *Institute of Chemistry, Vladivostok USSR; J. Anal. Chem. USSR*, vol. 41, No. 6, pp. 792–796, Abstract Only (Nov. 1986).

Hamburg Univ (Germany), "Circulation and Pollutant Turnover in the North Sea, Final Report," *Bundesministerium fuer Forschung and Technologie*, Bonn, Germany, No. T 2351, 193p, Abstract Only (Apr. 1990).

Harasawa, S.H., et al., "Monitoring of Neutron Fluence Rate by Capture Gamma Rays for Boron Neutron Capture Therapy," *Proceedings of First Asian Symposium on Research Reactors*, pp. 291–296 Abstract Only (Nov. 18, 1986).

Hearn, R.A., et al., "Remote Measurement of Coolant and Effluent Parameters in Operating Nuclear Power Plants," *IEEE Trans. Nucl. Sci*, vol. 30, No. 1, Abstract Only (Feb. 1983).

Hearst, J.R., et al., "In–Situ Equivalent $CO_2$ Estimates Using a Neutron–Induced Gamma–Ray Spectroscopy Logging System," *Symp. on Containment of Underground Nuclear Explosions*, Santa Barbara CA pp. 160–186, Abstract Only (Sep. 19–21, 1989).

Hilditch, P.I., et al., "Disposable Electrochemcial Biosensors," *Analyst*, p. 1217, Abstract Only (Dec. 1991).

Davy, D.R., "Freewater Mussel, Velesunio Angasi —a Monitor for Radium–226 Pollution in the Alligator Rivers Region, Northern Territory," Australian Atomic Energy Comm., Research Est., Lucas Heights, Darwin, North Territory, Australia, Abstract Only (Jul 9, 1984).

Dotson, D.W., et al., "In–Situ Tritium Borchole Probe for Measurement of Tritium," U.S. 4,464,338, Dept. of Interior, filed Oct. 24, 1980, Abstract Only (Aug 7, 1984).

Duray, J.R., et al., "Nonintrusive and Intrusive Sensing of Environmentally Important Objects," Proc. of the Information Exchange Meeting on Characterization, Sensors and Monitoring Technologies, U.S. DOE Information Exchange Meeting, Dallas, TX (USA) Abstract Only (Jul. 15–16, 1992).

Durler, D.L., et al., "In–situ Uranium Leach Mining: Considerations for Monitor Well Systems," U.S. Steel Corp. Soc. of Petr. Eng., Dallas TX (USA) Abstract Only (Sep. 21, 1980).

Derwent Publ., WPI 75–60813W/37; Patent assignee, Environm Sci Assoc (Abstract Only) Month Unavailable.

Edlund, David, et al., "Thin–Film Polymetric Sensors for Detection and Quantification of Multivalent Metal Ions," *Bend Research, Inc.*, Bend, Oregan USA, *Sensors and Actuators*, vol. B10 pp. 185–190 Abstract Only (Feb. 3, 1993).

Euromar Project "Mermaid," Bopnn, Germany, Abstract Only (Mar. 1991).

Fischer, K.P., et al., "Field Testing of Deep Water Cathodic Protection on the Norwegian Continental Shelf," Norwegian Marine Technology Res. Int., Abstract Only (Jan. 1988).

Gil, E.P., et al., "Potentiometric Stripping Determination of Mercuty (II), Selenium (IV), Copper (II) and Lead (II) at a Gold Film Electrode in Water Samples," *Analytica Chimica Acta*, vol. 293 pp. 55–65 Abstract Only (Jan. 1994).

Bonakdar, J.L., "Bioamperometric Sensors for Phenol Based on Carbon Paste Electrodes," *J. Electroanal. Chem.*, vol. 266, pp. 47–55 Abstract Only (Feb. 1989).

Bueker, H., et al., "Elcobox I," Nuclear Research Center, Juelich, Ann. Meeting of Inst. of Nuclear Materials Management, Albuquerque NM USA, Abstract Only (Jul. 21, 1985).

Campanella, L., "Determination of Phynol in Wastes and Water Using an Enzyme Sensor," *Analyst*, vol. 118, Abstract Only (Aug. 1993).

Cervinka, J., et al., "Equipment for Monitoring Process of Burning of Water or Water Vapor in Liquid Sodium, and of Materials Entrainment Due to This Burning," Abstract Only (Feb. 1, 1983).

Chan, S.S., et al., "In Situ Laser Raman Spectroscopy: Comparison," Pittsburgh Conf. and Exp. on Analytical Chem. and applied Spectroscopy, Atlantic City NJ USA Abstract Only (Mar. 10, 1986).

Chudyk, W.A., "Remote Detection of Groundwater Contaminants Using Far–Ultraviolet Laser–Induced Fluorescence," *Anal. Chem.*, vol. 57, No. 7, pp. 1237–1342 (Jun. 1985).

Cole–Palmer, Advertisement, "Oakton ElectraScan EC–1 Series," brochure Feb. 1991.

D'Silva, A.P., et al., "Remote, Real–Time Analysis of Hazardous Wastes Through Laser Ablation–Inductively Coupled Plasma Atomic Emission Spectrometry," Proc. of the Information Exchange Meeting on Characterization, Sensors, and Monitoring Technologies, US DOE/Dallas TX (USA) Abstract Only (Jul. 15–16, 1992).

Daniels, J.I., et al., "Evaluation of Military Field–water Quality," *Final Report, vol. 9, Data for Assessing Health Risks in Potential Theaters of Operation for US Military Forces*, Lawrence Livermore National Lab CA (USA) Abstract Only (Feb. 1988).

Adam, K., "Field Method for Determination of Surface Contamination Density," Int'l Conf. on Nuclear Spectroscopy and Nuclear Structure, (Apr. 16–19, 1991).

Aldstadt, J.H., "Determination of Heavy Metals by Thin Layer Chromatography–Square–Wave Anodic Stripping Volta," *Anal. Chem.*, vol. 64, pp. 3176–3179 (Dec. 1992).

Analytical Chemistry, "Blood Lead Measurement Takes the Direct Approach," *Analytical Chem.*, vol. 65, No. 5, p. 265A (Mar. 1, 1993).

Arnold, M.A., "Fiber–Optic Chemical Sensors," *Anal. Chem.*, vol. 64, No. 21, p. 1015A, Abstract Only, (Nov. 1, 1992).

Asher, J.C., "Experience of Plant Corrosion Monitoring by Thin Layer Activation," Proc. of Tech. Symp. of Corrosion '86, Abstract Only, Houston TX USA (Mar. 17, 1986).

Atomic Energy of Canada, Ltd., Progress Report, Health Sciences Div., Chalk River Nuclear Labs, Abstract Only, (Nov. 1980).

Auxier, J.A., et al., "Industrial Safety and Applied Health Physics Div. Annual Report for 1981," Oak Ridge National Lab, TN (USA) Abstract Only, (Aug. 1982).

Balogh, K., "Comparison of Mussels and Crustacean Plankton to Monitor Heavy Metal Pollution," *Balaton Limnological Res. Inst., Hungarian Acad. Sci.*, Tihany, Hungary, vol. 37, No. 3–4, pp. 281–292 Abstract Only (1988).

Bastiaans, G.J., et al., "Chemical Sensors Technology Development Planning Workshop," Ames Lab., Abstract Only (Mar. 1993).

Birge, W.J., "Embryo–Larval Bioassays on Inorganic Coal Elements and In Situ Biomonitoring of Coal–Waste Affluents," Univ. of Kentucky, Lexington USA, Abstract Only (Dec. 3, 1978).

Wang, J., et al., "Remote Electrochemical Sensor for Trace Metal Contaminants," *Anal. Chem*, vol. 67, No. 8 (Apr. 15, 1995) pp. 1481–1485.

Wang, J., "Remote Electrochemical Sensors for Monitoring Inorganic and Organic Pollutants," *Trends in Amnal. Chem.*, vol. 16, No. 2, (1977) Month Unavailable pp. 84–88.

RENEWABLE-REAGENT ELECTROCHEMICAL SENSOR

CROSS-REFERENCE TO RELATED APPLICATIONS

This application is a continuation-in-part application of U.S. patent application Ser. No. 08/383,717, entitled "Remote Electrochemical Sensor", to Joseph Wang, Khris Olsen and David Larsen, filed on Feb. 3, 1995, now U.S. Pat. No. 5,676,820, and the specification thereof is incorporated herein by reference.

GOVERNMENT RIGHTS

The U.S. Government may have rights to this invention and the right in limited circumstances to require the patent owner to license others on reasonable terms as provided for by the terms of U.S. Department of Energy (DOE) Grant No. DE-FG07-96ER62306, and by DOE Waste Management Education and Research Consortium (WERC).

BACKGROUND OF THE INVENTION

1. Field of the Invention (Technical Field)

The present invention relates to an electrochemical sensing apparatus and method for continuous monitoring of metals and organic compounds, by means of continuous circulation of reagent and repeated introduction of fresh reagent.

2. Background Art

Detection and monitoring of metals and organic compounds is normally done by having an operator collect on-site field samples and then taking the samples back to a laboratory.

Attempts have been made to provide both remote field sampling and analysis, on-site. See U.S. Pat. No. 5,120,421, entitled "Electrochemical Sensor Detector System and Method," to Glass et al., and U.S. Pat. No. 5,296,125, entitled "Electrochemical Sensor Detector System and Method" to Glass et al. However, an operator is still required to be present on-site to collect the sample, and the device does not communicate directly with the laboratory.

Contamination of hazardous sites and groundwater with toxic heavy metals (e.g., mercury (Hg), lead (Pb), uranium (U), arsenic (As), chromium (Cr), aluminum (Al)) represents a major national problem. Site monitoring and surveillance programs are required for a closer control of metal pollutants. The traditional use of atomic-spectroscopy central-laboratory measurements of heavy metals is too expensive and time consuming. Also, samples often change composition during their collection, transport and delay before analysis, ultimately producing unreliable results. Innovative field deployable methods are highly desired for the task of site characterization and remediation, as they minimize the huge labor analytical costs, and provide timely data for real-time emergencies and decision making. Chemical sensors are particularly attractive for providing real-time, remote monitoring of priority pollutants. While fiber-optic probes have been suggested for monitoring organic contaminants, no chemical sensor technology has demonstrated capability for remote monitoring of trace metals. (See W. Chudyk, et al., J. Anal. Chem. 1985, 57, 1237.) Clearly, a cost effective metalsensor technology, capable of monitoring the metal both in time and location, is needed to support the characterization and remediation of hazardous waste sites. (See G. Batiaans et al., (Eds.), "Chemical Sensors: Technology Development Planning," U.S. Department of Commerce, Springfield, 1993.)

In the present invention, there is provided a sensor for in-situ monitoring of trace metals and organic pollutants. The sensor of the invention is designed both for remote, on-site, use or for use in laboratory applications. The compact instrumentation and low power needs of electrochemical techniques satisfy many of the requirements for on-site metal analysis. Particularly attractive for in-situ monitoring of metal contaminants is the remarkably sensitive technique of stripping analysis. (See J. Wang, "Stripping Analysis: Principles, Instrumentation, and Applications," VCH Publishers, Deerfield Beach, Fla. 1985). The extremely low (subanomolar) detection limits of stripping analysis are attributed to its "built-in" pre-concentration step, during which the target metals are deposited onto the working electrode. However, since the performance of stripping analysis as previously achieved, depends on the electrolytic plating of target metals onto the working electrodes of a sensor, conventional stripping analysis alone is not satisfactory for many environmentally-important metals that cannot be readily electroplated. Additionally, conventional stripping measurements, have suffered from interferences by surfactants (surface-active materials) commonly present in environmental samples that have passivated the electro-surface.

SUMMARY OF THE INVENTION (DISCLOSURE OF THE INVENTION)

One of the objectives of the present invention is to extend the concept of metal monitoring, either in remote or laboratory applications, and specifically in-situ electrochemical stripping sensors, toward environmentally significant metals that cannot be easily electro-deposited. Such extension is achieved by employing electrochemical monitoring/detection methods, e.g., adsorptive stripping procedures involving the formation and adsorptive accumulation of appropriate complexes of the target sample, and the delivery of a ligand solution through a microdialysis sampling tube, followed by transport of the resulting complex to a downstream detector. The use of alternative (nonelectrolytic) accumulation schemes offers great promise for monitoring priority metal pollutants, including uranium (U), chromium (Cr), nickel (Ni), cobalt (Co), aluminum (Al) or iron (Fe). To achieve this goal, renewable chemistry, involving controlled, continuous reagent (ligand) delivery, is utilized in a manner analogous to that employed in renewable fiber-optic devices.

Accordingly, the preferred sensor of the invention is an electrochemical sensing apparatus comprising an electrode, means for continuously circulating a reagent while reacting said reagent and an analyte proximate said electrode, and means comprising a membrane for ingress of said analyte. The electrode may further comprise a working electrode that is a bare or mercury-coated solid electrode (carbon, gold, platinum, iridium). The working electrode may still further comprise a glassy carbon Hg-coated solid electrode. The reagent may comprise an enzyme or a biologically or chemically modified molecule (utilizing a biological or chemical species).

The means of continuously circulating a reagent further comprises means comprising reagent delivery inlet and outlet tubes, or further comprises a pump. The means comprising a membrane further comprises reagent delivery inlet and outlet tubes. The analyte further comprises inorganic (metal) pollutant substrates, such as uranium (U), chromium (Cr), nickel (Ni), cobalt (Co), aluminum (Al) or iron (Fe), or numerous organic compounds that react with the reagent to produce an easily detected electro-active species. Additionally, the membrane inhibits entry of macromolecular surfactants that may passivate the surface.

The preferred method of the invention is an electrochemical method of detecting metal and organic pollutants in analytes comprising the steps of providing an electrode, continuously circulating a reagent while reacting the reagent with an analyte proximate the electrode, and providing a membrane for ingress of the analyte. The step of providing an electrode further comprises the step of providing a working electrode; and the step of providing a working electrode further comprises a step of providing a bare or Hg-coated solid electrode (of carbon, gold, platinum or iridium), a glassy carbon mercury-coated electrode, or a modified electrode utilizing a biological or chemical species. The step of continuously circulating reagent further comprises the step of providing reagent delivery inlet and outlet tubes. The step of providing a membrane further comprises the step of providing reagent delivery inlet and outlet tubes.

A primary object of the present invention is the detection of environmentally important trace metals and/or organic pollutants that are not readily electroplated.

Another object of the invention is the continuous delivery of reagent and sample to the working electrode.

Still another object of the invention is the prevention of surfactant permeation and hence surface passivation.

A primary advantage of the present invention is the combination of ligand delivery through microdialysis sampling tubes.

Another advantage of the present invention is the relative ease of cleaning electrodes and introducing fresh reagent (ligand) solution.

Yet another advantage of the present invention is its adaptability to detection of nonelectroactive organic pollutants, via reaction with a flowing redox marker.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

(BEST MODES FOR CARRYING OUT THE INVENTION)

The invention comprises a renewable-reagent sensor designed to accommodate an electrochemical detecting process, for example, the complex formation and adsorptive accumulation steps of adsorptive stripping protocols, for monitoring environmentally-important metals that are not readily electroplated. The flow probe of the invention relies on the delivery of a ligand solution through a microdialysis sampling tube, followed by transport of the resulting complex to a downstream detector. The microdialysis sampling step minimizes the interference of surface-active macromolecules and extends the linear dynamic range compared to conventional electrochemical, e.g., adsorptive stripping, measurements.

Figure 1:
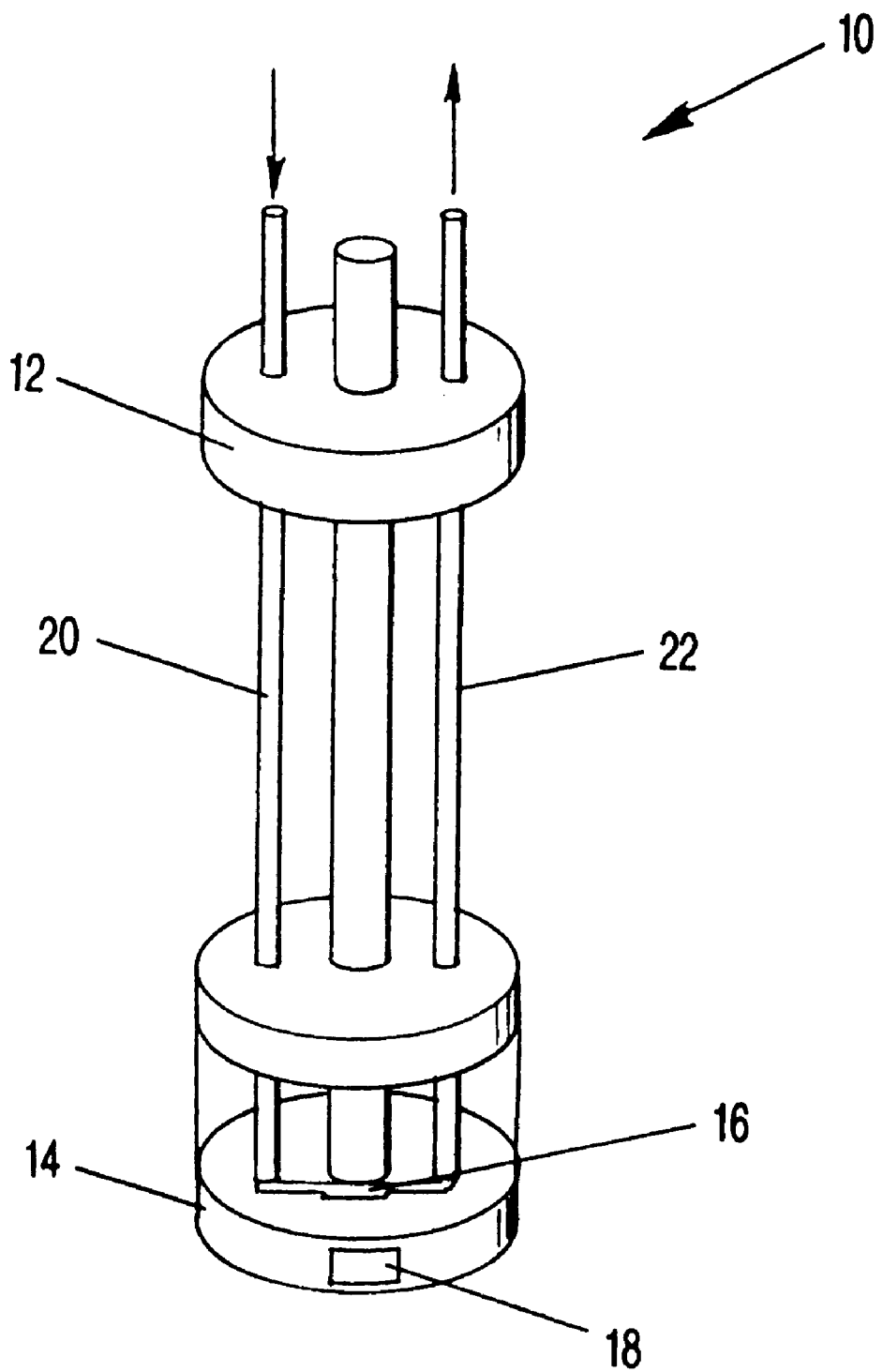
FIG. 1 is a schematic diagram of the preferred renewable-ligand electrochemical sensor of the invention.

As schematically depicted in FIG. 1, the preferred flow probe 10 of the invention comprises Plexiglas housing 12. Accommodated within probe 10 is a glassy carbon disk or solid working electrode 14 which may be bare or mercury-coated. Working electrode 14 is positioned within channel 16 at the base of probe 10. A Vycor disk 18 may also be positioned at the base of probe 10 to provide an external conductive connection. In an actual field sampling situation, Ag/AgCl and Pt reference and counter electrodes (not shown) would also be provided within channel 16.

Dialysis sampling tube 20 and Teflon drainage capillary 22 are fixed to apertures in probe 10; a portion of probe 10 is removed to accommodate these tubes. The inlet of dialysis tube 20 is connected to a microsyringe pump (not shown) to provide continuous reagent flow capability. Sampling of analyte occurs by means of permeation through dialysis tube 20.

In operation, ligand solution delivered through dialysis tube 20 reacts with the permeating analyte in dialysis tube 20. The resulting complex is transported to channel 16 and working electrode 14 and there accumulated. Detection of the trace metal is then effected by a chosen mode of electrochemical analysis, such as chronopotentiometric or voltammetric analysis. The renewable-reagent electrochemical sensor, shown in FIG. 1, relies on continuous delivery of the ligand to the working electrode 14, its complexation reaction with the "metal collected" in the dialysis sampling tube, transport of the complex to the working-electrode 14 in compartment 16, and electrochemical (e.g., chronopotentiometric or voltammetric) detection of the accumulated complex. The detection step, or the separate cleaning step, remove the chemical complex from the surface to allow drainage through the outlet capillary 22.

The integrated membrane-sampling/electrochemical sensor of the invention was tested in connection with the monitoring of trace uranium and nickel using propyl-gallate (PG) and dimethylglyoxime (DMG) chelating agents. In these tests, established adsorptive stripping protocols for trace uranium and nickel, based on complexation with PG and DMG, respectively, were used for characterizing and testing stripping probe 10 of the invention. Experimental variables, including reagent delivery rate and ligand concentration, were explored in the testing.

Figure 2A:
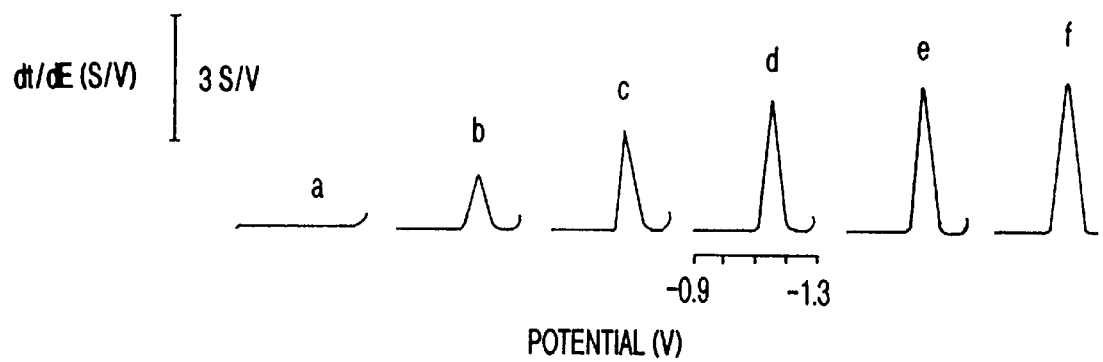
FIGS. 2(a) and (b), respectively, are chronopotentiograms for 117 $\mu$g/L nickel and 1000 $\mu$g/L uranium with various times and potentials.
Figure 2B:
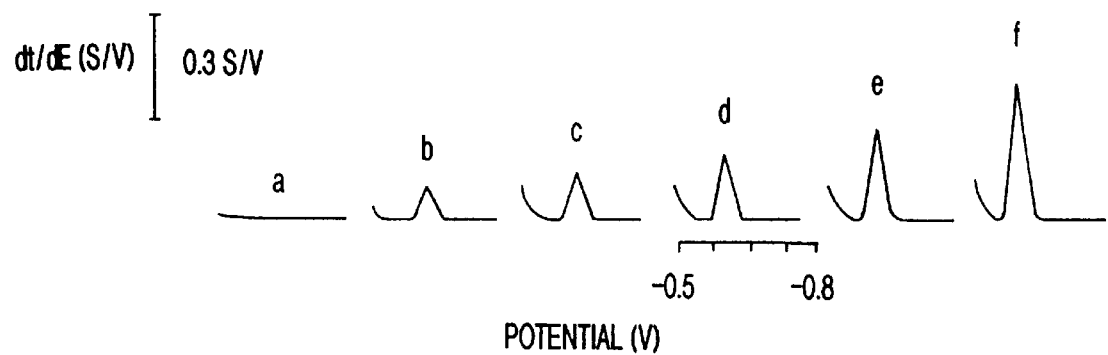

FIG. 2 displays chronopotentiograms for non-deaerated solutions of 0.12 mg/L nickel (FIG. 2(a)) and 1.0 mg/L uranium (FIG. 2(b)), obtained with the flow probe, following different adsorption times (0–150 seconds, a–f). The nickel/DMG and uranium/PG chelates yield well-defined reduction peaks at −1.14 V and −0.63 V, respectively. The longer the accumulation time, the more complex is adsorbed onto the working electrode, and the larger is the peak height. While the nickel peak rises rapidly with the time at first and then more slowly, the uranium signal increases over the entire time scale tested. Convenient measurements at the mg/L level are thus feasible following very short (1–2 minute) accumulation periods. No response is observed without the adsorptive accumulation. The favorable background response, obtained for non-deaerated samples, eliminates the need for a time-consuming deaeration step, hence making the chronopotentiometric stripping mode attractive for potential field applications. A short "cleaning" period (at −1.4 V FIG. 2(a)) or −1.5 V FIG. 2(b)) is sufficient for desorbing the complex prior to the next measurement.

Figure 3A:
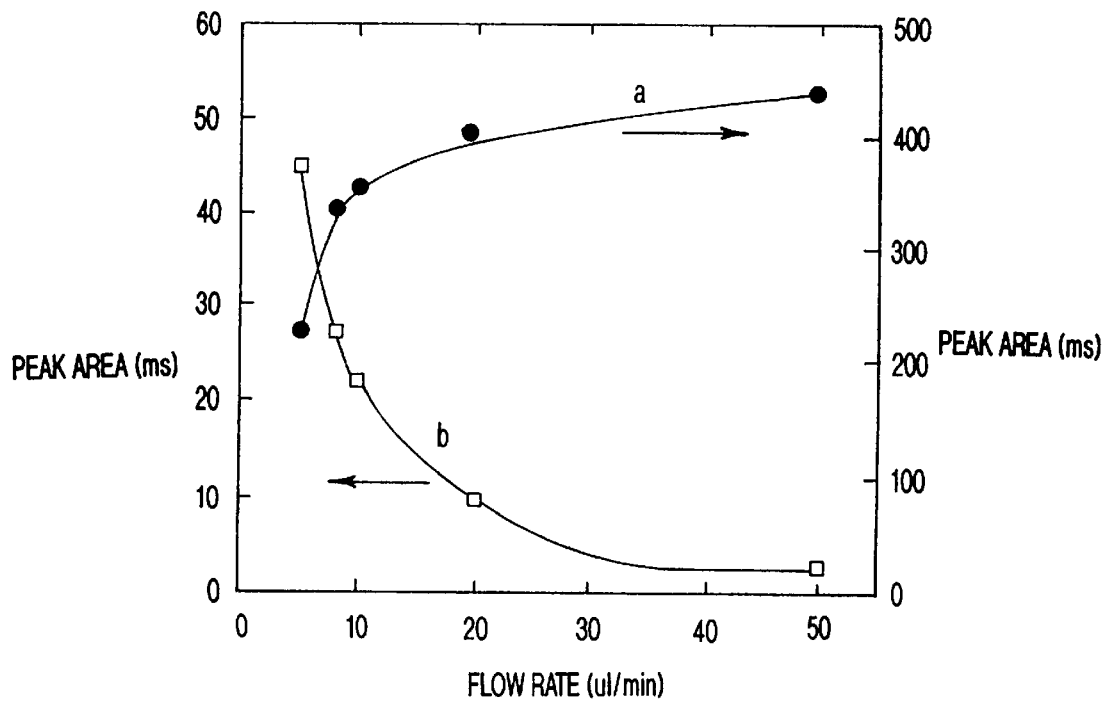
FIGS. 3(a) and (b), respectively, represent the effect of delivery (flow) rate and ligand concentration on nickel (a) and uranium (b) signals.

The influence of various experimental variables affecting the response of the renewable-reagent sensor was tested. FIG. 3(a) shows the dependence of the adsorptive stripping response of nickel (FIG. 3(a)) and uranium (FIG. 3(b)) on the flow rate of the reagent solution. Different profiles are observed for these metals. While the nickel response increases rapidly upon raising the flow rate between 5 and 10 min and then more slowly, the uranium signal decreases sharply upon increasing the flow rate. Such different profiles are attributed to the fact that the reagent-solution flow rate affects (in a different fashion) various steps of the sensor operation, including the metal sampling, the complex formation and adsorptive accumulation. Obviously, the target metal and the ligand used have a profound effect upon the transport rate through the membrane and upon the rate of the complex formation (leading to different flow rates effects for the different metals).

Figure 3B:
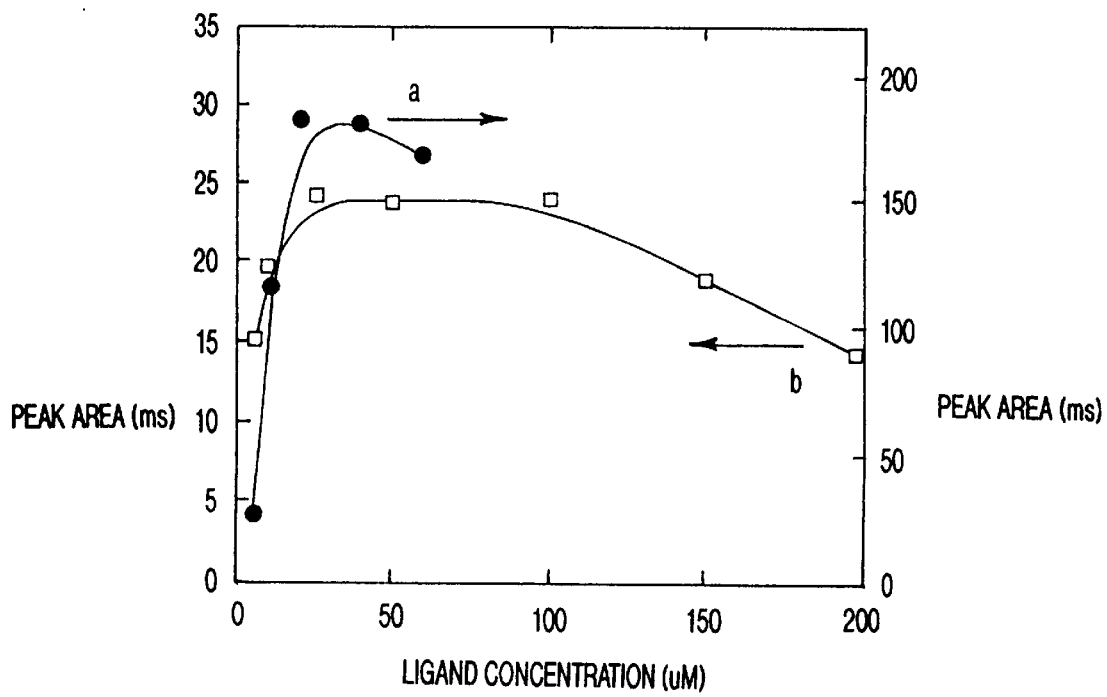

The influence of the ligand concentration (in the receiving solution) is shown in FIG. 3(b). For both nickel (a) and uranium (b), the response rises sharply (to a steady-state value) with the ligand concentration at first, and then decreases slowly. Compared to conventional adsorptive stripping measurements, the ligand and its level affect the response also through their influence on the microdialysis collection of the target metal.

Figure 4A:
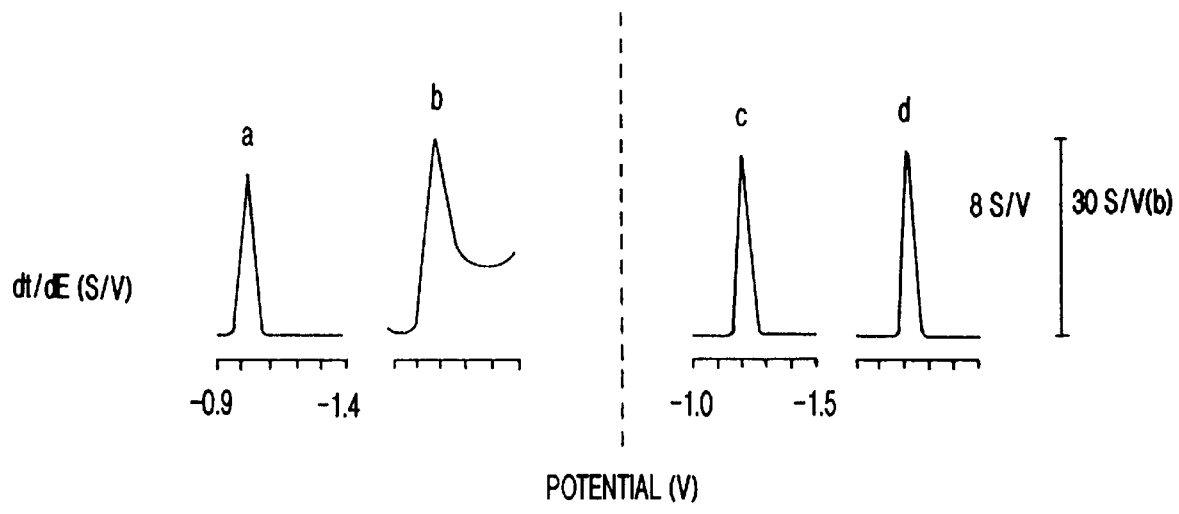
FIGS. 4(a), (b), and (c), respectively, represent the effect of dodecyl sodium sulfate and Triton X-100 on the nickel stripping signal, and the effect of Arabic gum on the uranium response.
Figure 4B:
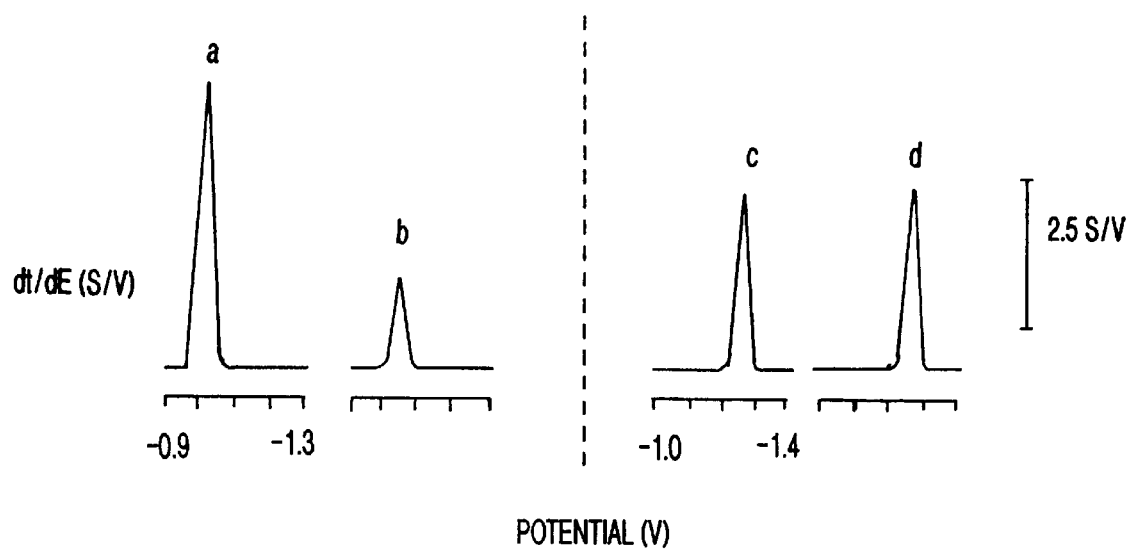
Figure 4C:
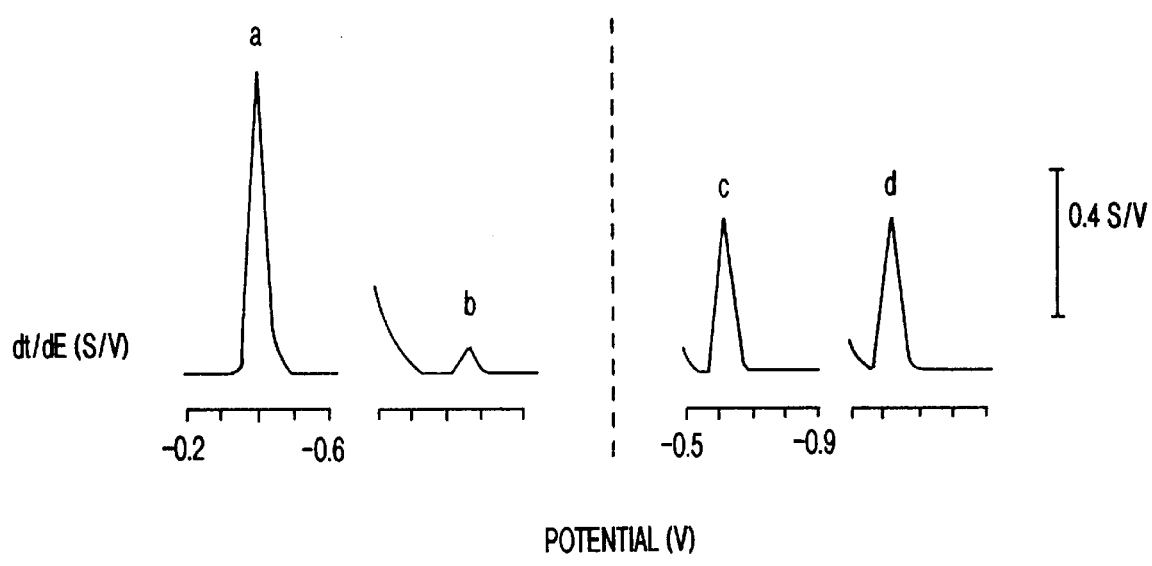

Electrochemical, particularly adsorptive stripping, measurements commonly suffer from interferences by surface-active materials present in environmental samples. Using adsorptive stripping measurements as the example, such substances have a marked effect on the adsorptive stripping response owing to competitive adsorption for surface sites. The microdialysis sampling of the renewable sensor greatly minimizes such matrix effects. Because the membrane does not favor permeation of large macromolecules, the flow probe offers good resistance to surfactant effects. Such resistance is illustrated in FIG. 4. Conventional adsorptive stripping measurements (on the left side of the Figures) result in a substantial depression of the nickel (FIG. 4(b)) and the uranium (FIG. 4(c)) peaks following the addition of Triton X-100 and Arabic gum (compare a and b). In addition, the presence of dodecyl sodium sulphate causes a severe distortion of the nickel peak (FIG. 4(a)). In contrast, no change of the nickel or uranium is observed at the renewable-reagent sensor of the present invention in the presence of similar levels of these surfactants (on the right side of the Figures).

Figure 5A:
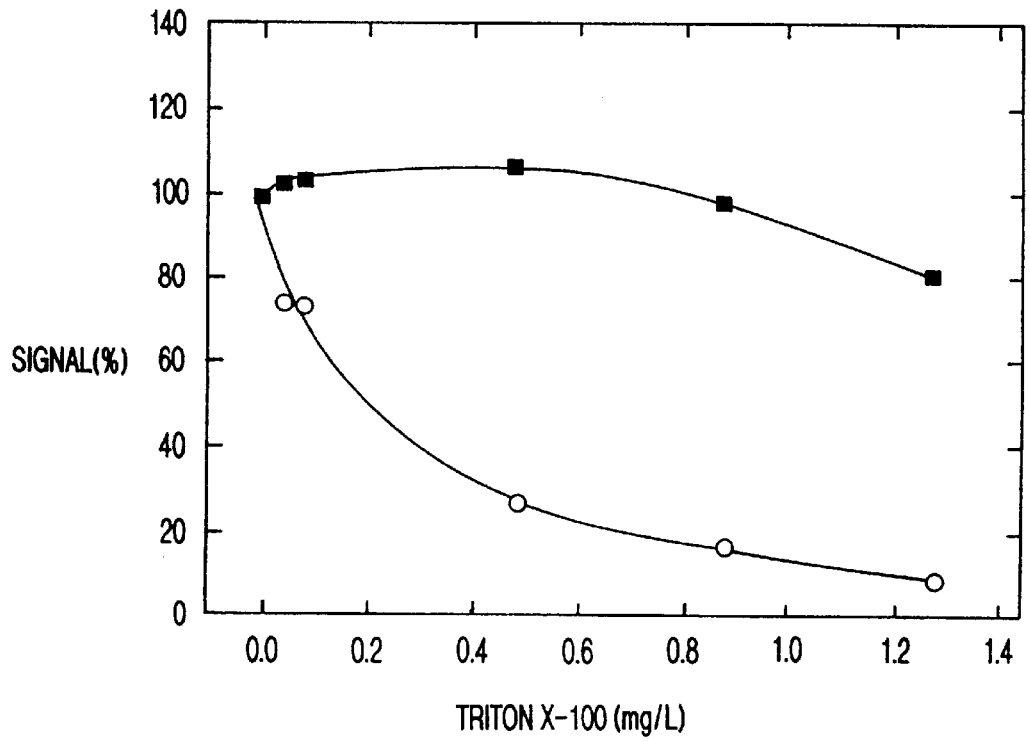
FIGS. 5(a) and (b), respectively, represent the effect of surfactant on nickel and uranium measurements in the sensor having a dialysis membrane.
Figure 5B:
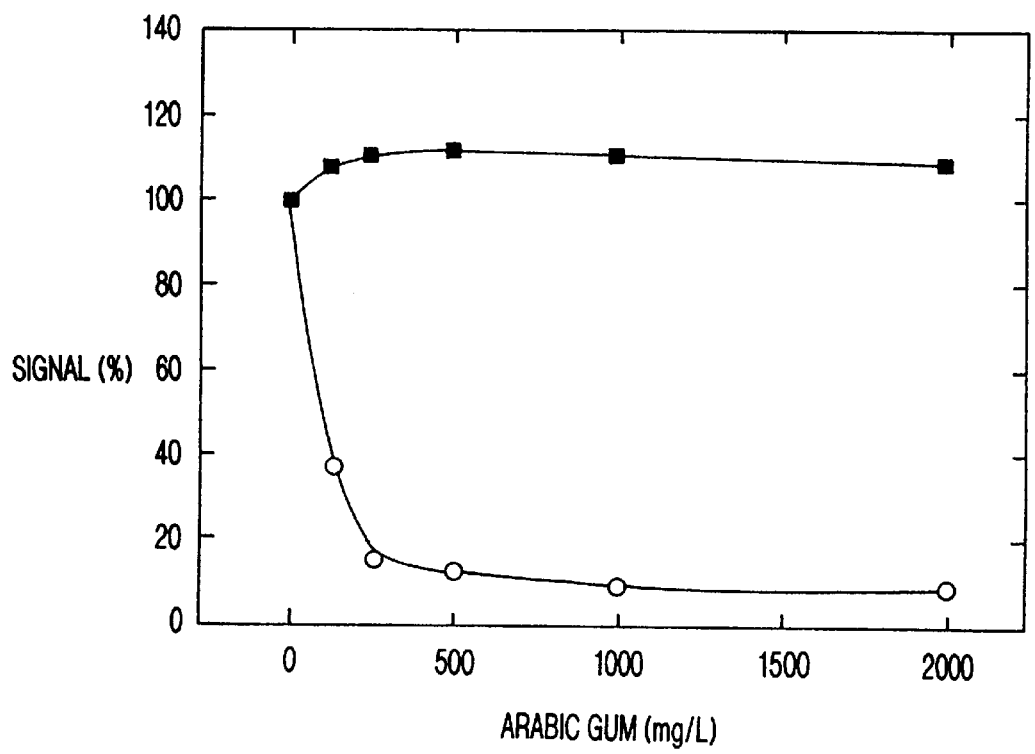

Such protective action is illustrated also in FIG. 5. Using the conventional stripping protocol (b), the nickel (FIG. 5(a)) and uranium (FIG. 5(b)) peaks decrease rapidly upon raising the surfactant concentration (with 90% depressions at 1.3- and 1000 mg/L Triton X-100 and Arabic gum, respectively). In contrast, the flow probe offers a highly stable uranium response up to 2000 mg/L Arabic gum (FIG. 5(b)-a). The nickel peak is also not affected by the Triton X-100 concentration up to 0.9 mg/L, but displays a 20% loss at 1.3 mg/L Triton X-100 (FIG. 5(a)-a).

Figure 6A:
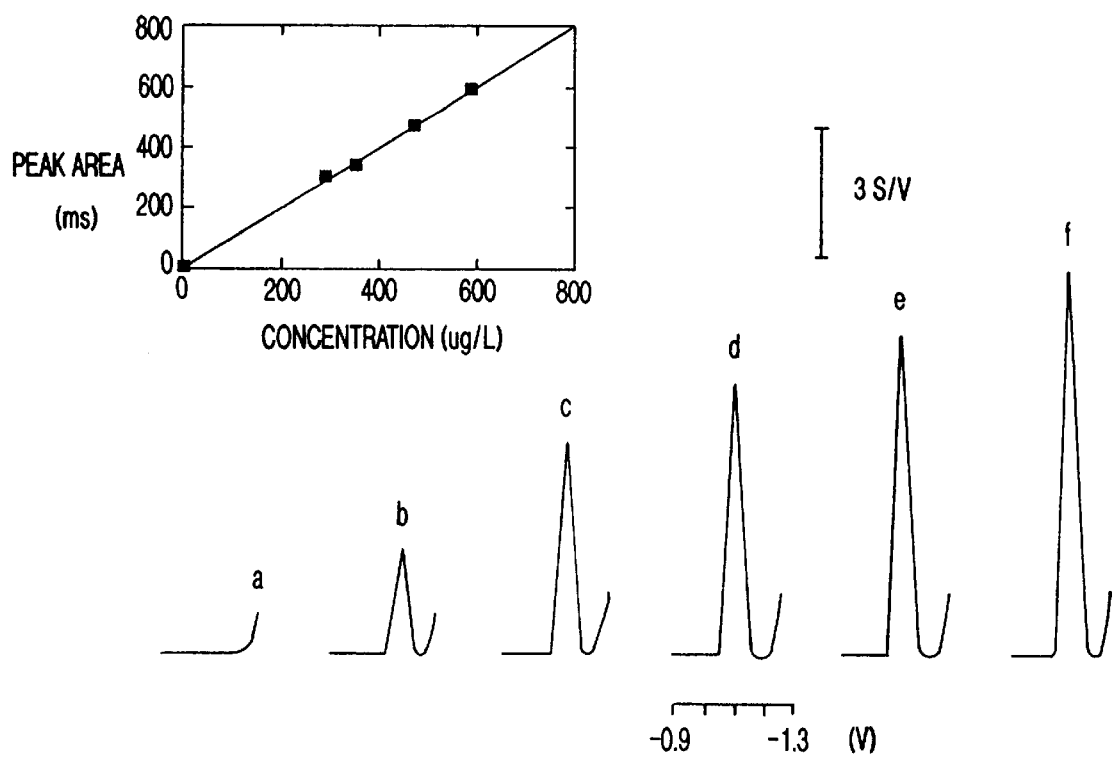
FIGS. 6(a) and (b), respectively, represent potentiograms of uranium and nickel with increasing concentrations.
Figure 6B:
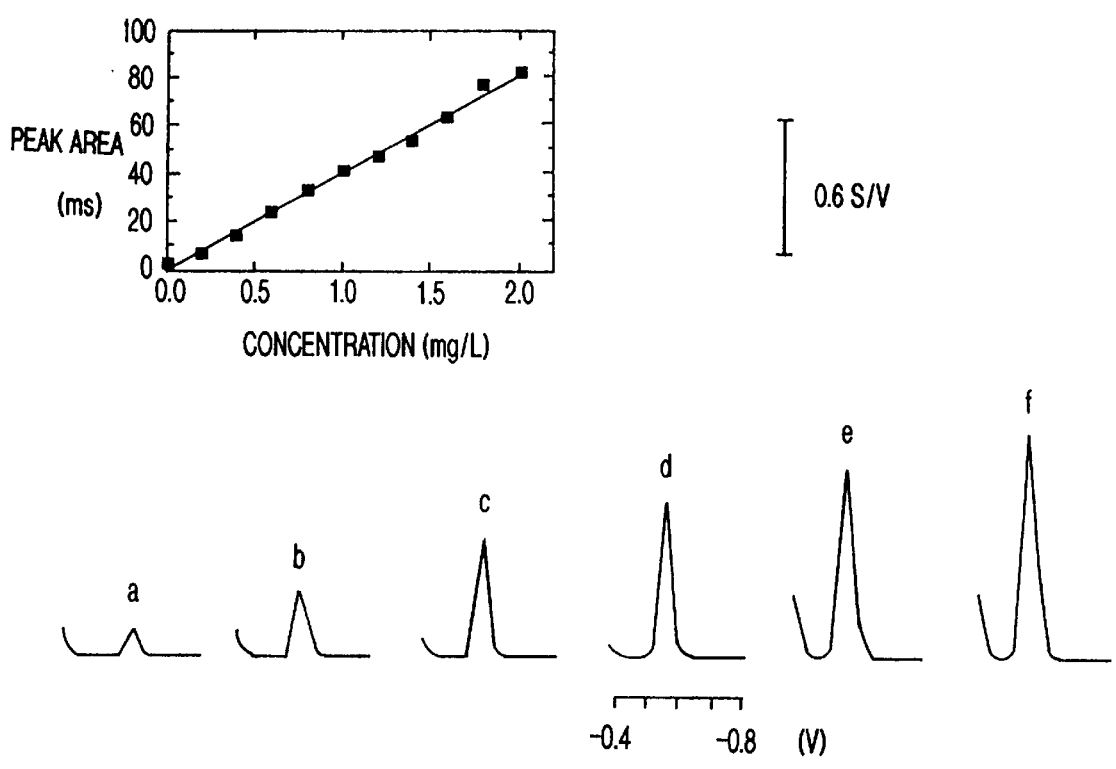

The renewable-reagent electrochemical sensor also displays a well-defined concentration dependence. FIG. 6 shows stripping potentiograms obtained for nickel (FIG. 6(a)) and uranium (FIG. 6(b)) solutions of increasing concentrations (60–300 $\mu$g/L and 200–1200 $\mu$g/L, respectively). The defined peaks observed over these ranges offer convenient quantitation following 2 (FIG. 6(a)) and 4 (FIG. 6(b)) minute adsorption. The six measurements shown in FIG. 6 are a part of 8 (FIG. 6(a)) or 10 (FIG. 6(b)) concentration increments up to 600 and 2000 $\mu$g/L, respectively. The resulting calibration plots are also shown in the Figures. For both metals, a linear relationship exists between the peak area and the bulk concentration over the entire ranges examined. Least-squares treatment of these data yields slopes of 1.025 (FIG. 6(a)) and 0.041 (FIG. 6(b)) ms.L/$\mu$g (correlation coefficients, 0.999 (FIG. 6(a)) and 0.997 (FIG. 6(b)). Apparently, conditions of low surface coverage (linear adsorption isotherms) exist. The very wide linear range (compared to conventional adsorption stripping measurements) is attributed to the "built-in" dilution action associated with the microdialysis sampling.

An analogous conventional (batch) adsorptive stripping calibration experiment for uranium yielded a nonlinear calibration plot, with a leveling off at 600 $\mu$g/l; the sensitivity (slope of the linear portion) was 20-fold higher than that of the flow probe. The different sensitivities observed with the renewable-reagent sensor for uranium and nickel are attributed in part to their different transport rates through the microdialysis membrane (with a more facile collection of the smaller nickel ion). The use of sampling membranes with higher molecular weight cutoffs would increase the recovery of the target metals, and would further enhance the sensitivity. In addition, the sensitivity and the dynamic range may be changed by adjusting the ligand delivery rate or the ligand concentration.

Figures 7A, 7B:
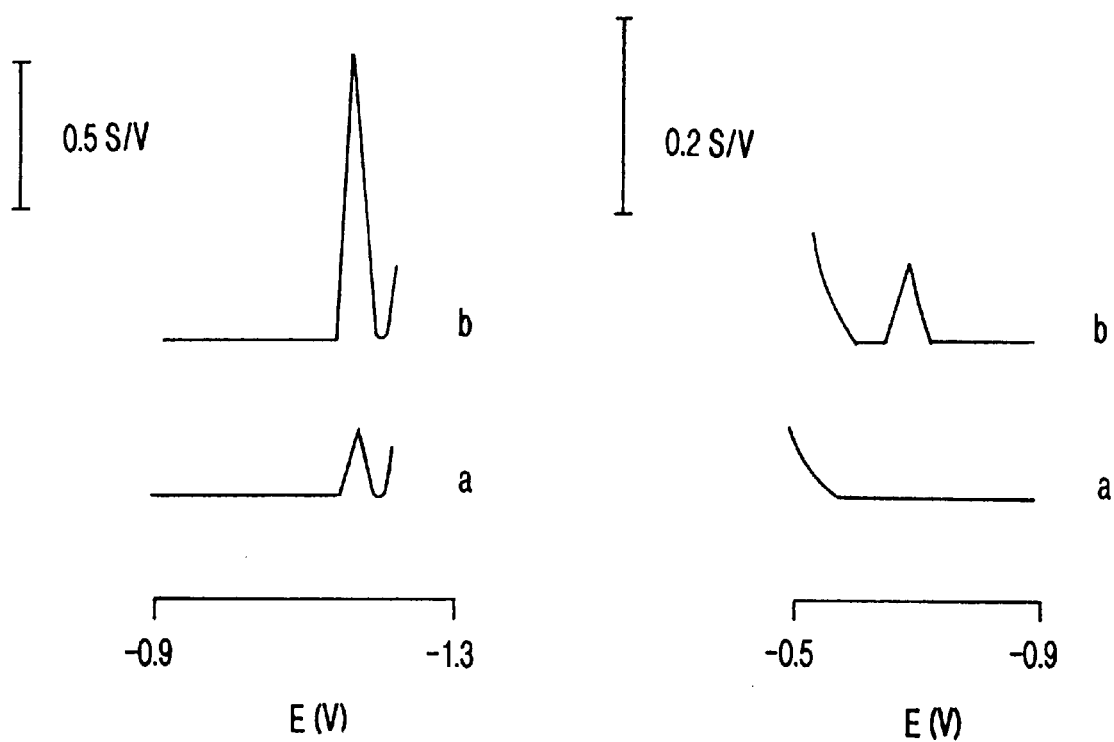
FIGS. 7(a) and (b), respectively, represent adsorptive stripping responses for 8 $\mu$g/L nickel (A,b) and 25 $\mu$g/L uranium (B, b).

Despite internal dilution, the renewable-flow probe 10 of the invention results in extremely low detection limits. These were estimated from the adsorptive stripping response for 8 $\mu$g/L nickel and 25 $\mu$g/L uranium (FIG. 7(a) and 7(b), respectively). Well defined peaks are observed for these low levels following 5 and 20 minutes accumulation(FIG. 7(a) and 7(b), respectively). Detection limits of 0.9 $\mu$g/L (1.5× $10^{-8}$ M) nickel and 10 $\mu$g/L (4.2×$10^{-8}$ M) uranium were estimated from the signal-to-noise characteristics of these data (S/N=3). Even lower detection limits are expected with longer accumulation times, use of more permeable membranes or in connection to a stopped-flow operation.

Figure 8A:
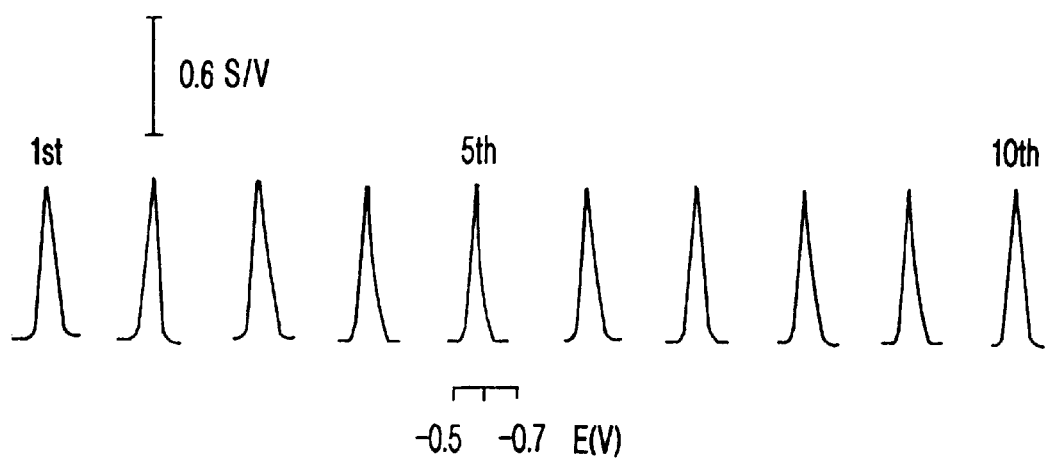
FIGS. 8(a) and (b), respectively, represent ten repetitive measurements of 117 $\mu$g/L nickel and 1000 $\mu$g/L uranium.
Figure 8B:
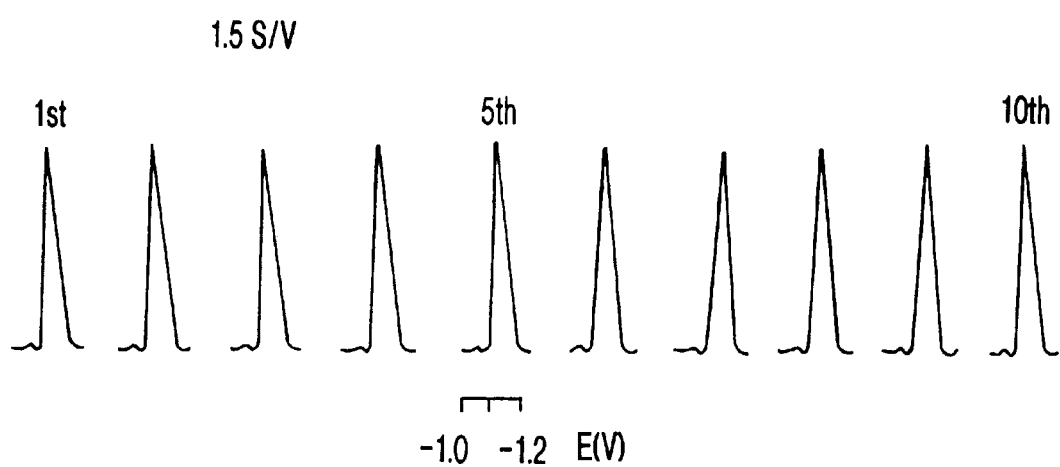

The renewable-ligand electrochemical sensor yields a reproducible and stable response. FIG. 8 displays stripping potentiograms for 10 repetitive measurements of uranium (FIG. 8(a)) and nickel (FIG. 8(b)). The peak area and shape are maintained throughout these operations, yielding relative standard deviations of 4.0% (FIG. 8(a)) and 3.7% (FIG. 8(b)). High stability (RSD=1.7%) was observed also in a longer (60 minutes) unbroken series involving 20 successive measurements of 400 μg/L nickel after a 2 minute accumulation (not shown). Such data reflect the efficiency of the electrochemical "cleaning" step, i.e., regeneration of a "metal-free" surface prior to each run.

Figure 9A:
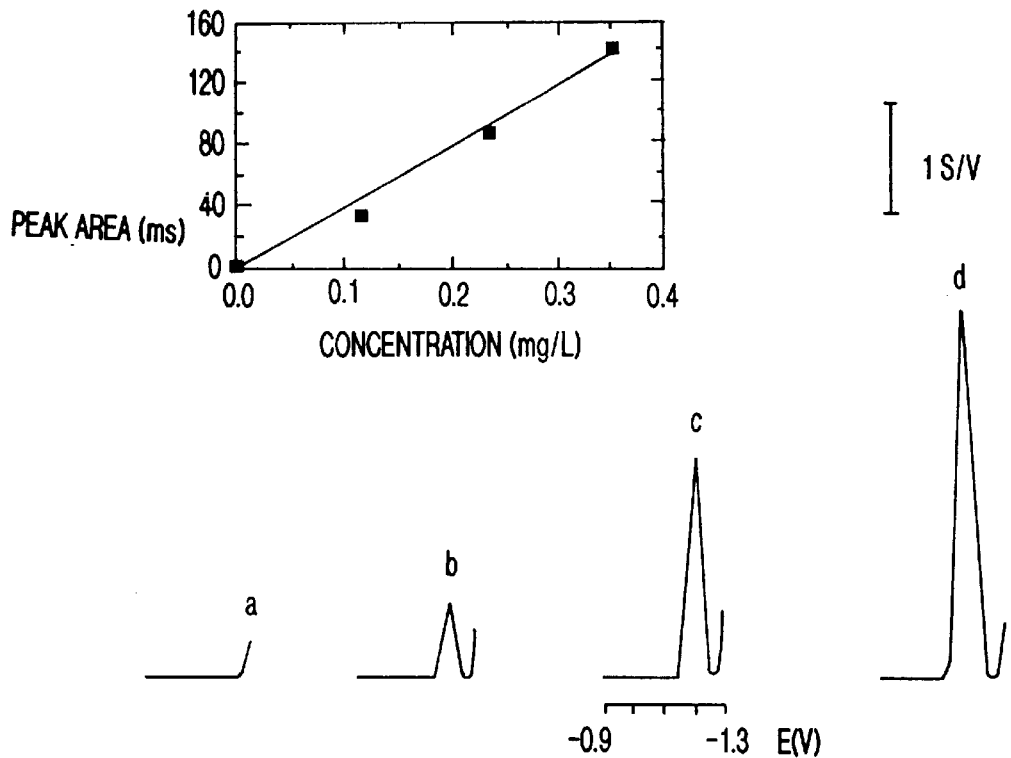
FIGS. 9(a) and (b), respectively, represent the stripping responses for a river water sample and for a groundwater solution spiked with increasing concentrations.
Figure 9B:
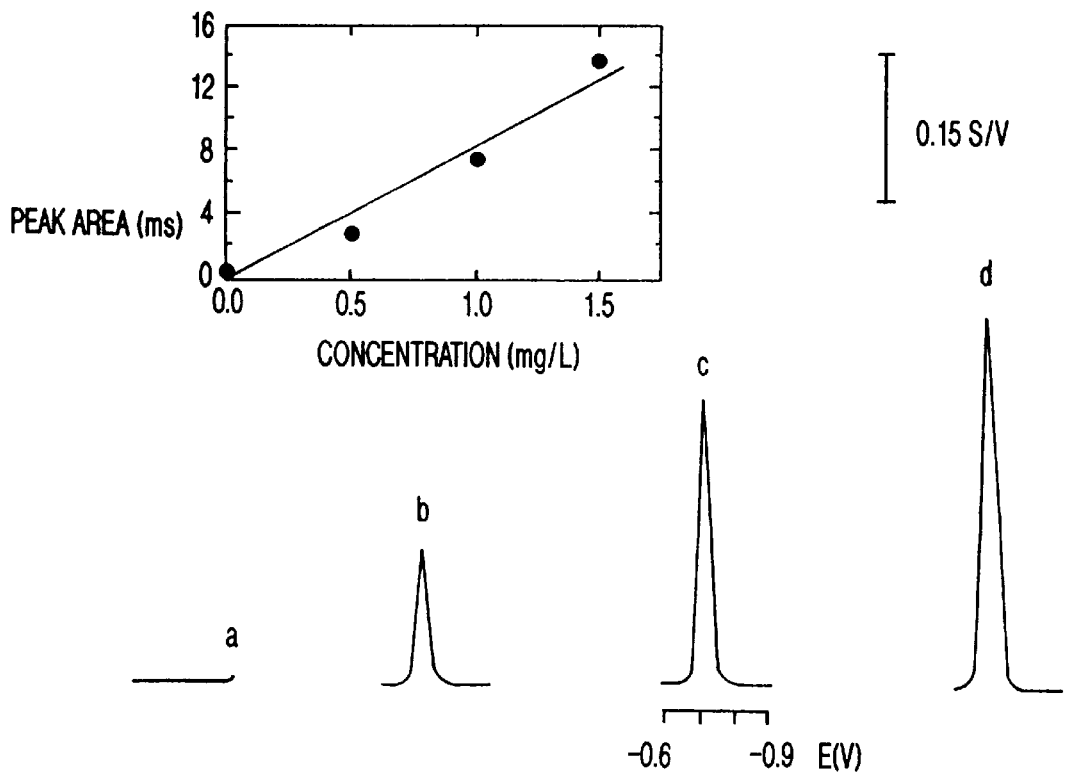

FIG. 9 demonstrates the applicability of the renewable-reagent sensor to measurements of trace metals in environmental samples. While no response is observed for the unpolluted river (FIG. 9(a)) or groundwater (FIG. 9(b)) samples, subsequent additions of 0.11 mg/L nickel (FIG. 9(a), b–d) or 0.5 mg/L uranium (FIG. 9(b), b–d) yielded defined adsorptive stripping peaks in connection with short accumulation times ( 2 and 3 minutes, respectively). No major interferences are indicated from the response of the unspiked sample.

It has been demonstrated that renewable-reagent flow probes are very suitable for adsorptive-stripping electrochemical sensing of trace metals. In summary, detection limits of $1.5 \times 10^{-8}$ M nickel and $4.2 \times 10^{-8}$ M uranium were obtained following 5-minute and 20-minute adsorption times, and a relative standard deviation of 1.7% was obtained for prolonged operations of, e.g., 20 runs.

Integration of microdialysis sampling with electrochemical, e.g., adsorptive stripping, detection extends the scope of electrochemical sensors to additional metals that are not readily electroplated. Near real-time monitoring of numerous metals can thus be accomplished via a judicious choice of the complexing ligand. The sensor of the invention is designed for laboratory use or for use in the field. The remote monitoring capability is coupled to minimization of interferences from surface-active materials and extension of the linear dynamic range (compared to conventional electrochemical, e.g., adsorptive stripping, measurements).

Integrating the reference and counter electrodes within the body of the flow probe, coupling the probe to a long shielded cable, and designing multichannel sensor arrangements for the simultaneous monitoring of several metals (with each channel carrying the desired complexation reaction) readies probe 10 for field detection. Considering the versatility of the renewable-flow electrochemical concept, probe 10 is easily adaptable to various environmental or industrial monitoring scenarios. The renewable-reagent electrochemical sensor is particularly applicable to assays of river and groundwater samples, and holds great promise for monitoring a variety of trace metals, either in the laboratory or remotely.

Conventional stripping measurements, that also suffer from interference of surfactants, may also benefit from the isolation of the target metals from large macromolecules. Other electrochemical detection schemes (e.g., biosensing of pollutants) may also benefit from the versatility of the renewable-reagent strategy.

Industrial Applicability

The invention is further illustrated by the following non-limiting examples.

Probe Design

The probe 10 is based on a Plexiglas cylindrical body 12 (0.8-inch diameter, 2-inch length) that accommodates the glassy carbon disk working electrode 14 and the reagent delivery and drainage capillaries, 20 and 22, respectively. The glassy carbon electrode 14 (Model MF-2012, BAS Inc.) was inserted through a 0.223-inch diameter hole drilled in the center of the Plexiglas cylinder 12. The electrode terminates in an 80 μL thin-layer channel 16 at the base of the sensor body, which formed by fixing (with epoxy) a plastic end cap. A 3-mm diameter Vycor disk 18 (BAS Inc.) was fixed at the center of the end cap, below the thin-layer channel 16, to provide conductivity to the external reference (Ag/AgCl) electrodes and Pt-wire counter electrodes (located in the sample solution). The dialysis sampling tube 20 and the Teflon drainage capillary 22 were fixed to holes in the Plexiglas body. A portion of the Plexiglas body was removed for accommodating these sampling and drainage tubes. A band of four "Regenerated Cellulose (RC) Hollow Fibers" (MWCO 13,000; 200-μm i.d.; Spectrum Medical Industries Inc.) serves for the dialysis sampling. Teflon tubing connects a microsyringe pump (2.5 mL volume, Model MD-100/MF-5127, BAS Inc.) with the inlet of the dialysis tubing. The outlet of the dialysis tubing is connected to the thin-layer working electrode channel 16 through a hole in the Plexiglas body.

Apparatus

Potentiometric stripping analysis (PSA) was performed with a TraceLab system (PSU20, Radiometer Inc.), in connection with an IBM PS/55XS (not shown).

Reagents

Stock solutions (1000 mg/L) of nickel and uranium (atomic adsorption standard, Aldrich) were diluted as required. DMG and PG were also received from Aldrich. A 0.02M ammonia buffer solution (pH 9.2) containing $5 \times 10^{-5}$ M DMG served as the receiving solution for the nickel system. A 0.05 M of acetate (Aldrich) buffer solution (pH 4.5) containing $1 \times 10^{-4}$ M PG was used for uranium measurements. Dodecyl sodium sulfate and Triton X-100 were obtained from J. T. Baker Chemical Co., and Arabic gum was obtained from Sigma. Rio Grande river samples were collected in Las Cruces, N. Mex., while the groundwater sample was collected at Hanford site (Richland, Wash.). Tap water samples were obtained at the NMSU laboratory. All solutions were prepared from double-distilled water. All chemicals used were analytical grade.

Procedure: Monitoring of Nickel

A Mercury film was preplated by immersing the polished glassy carbon disk electrode 14 in a 1mL cell containing a stirred 100 mg/L Hg and 0.1 M HCl solution, for 5 minutes while holding the potential at −0.6 V. Following the mercury deposition, the glassy carbon electrode 14 was incorporated into the flow probe body 10. The probe was then immersed into a 100 mL cell, containing 40 mL of a tap water solution. Adsorptive accumulation proceeded (usually for 2 minutes) while holding the potential at −0.7 V, and pumping the DMG/ammonia-buffer reagent solution at 10 μL/minutes. After the accumulation, the potentiogram was recorded by applying a suitable constant current. A "cleaning" step was followed by holding the sensor at −1.4 V for 10 seconds.

Procedure: Monitoring of Uranium

The glassy carbon based mercury film electrode was prepared using the procedure reported above for the measurement of nickel, prior to the uranium experiments, by preplating mercury at −0.6 V for 5 minutes from a 100 ppm Hg and 0.1M HCl solution. The coated electrode 14 was inserted into the flow probe body 10 and ready for use. The probe, along with the reference and counter electrodes, was then dipped in a 100 mL cell containing 40 mL of a 0.03 M NaCl solution. The reagent solution ($1 \times 10^{-4}$ M PG in 0.05 M acetate buffer solution, pH 4.5) was allowed to flow at 10 μl/minute, while applying an accumulation potential of −0.05 V for a selected time. After the accumulation step, a potentiogram was recorded by applying a constant negative current (−20 μA). The surface "cleaning" was carried out by holding the potential at −1.5 V for 60 seconds Following each addition, a 3-minute "waiting period" was used to allow for the microdialysis sampling and transport to the working-electrode compartment. All experiments were carried out at room temperature.

For comparison, conventional adsorptive stripping potentiometric measurements were carried out in a 10 mL cell (Model VC-2, BAS), using a stirred (ca. 500 rmp) sample solution, and accumulation periods, stripping currents and "cleaning" steps, similar to those using the flow probe.

Additional Embodiments

Figure 10:
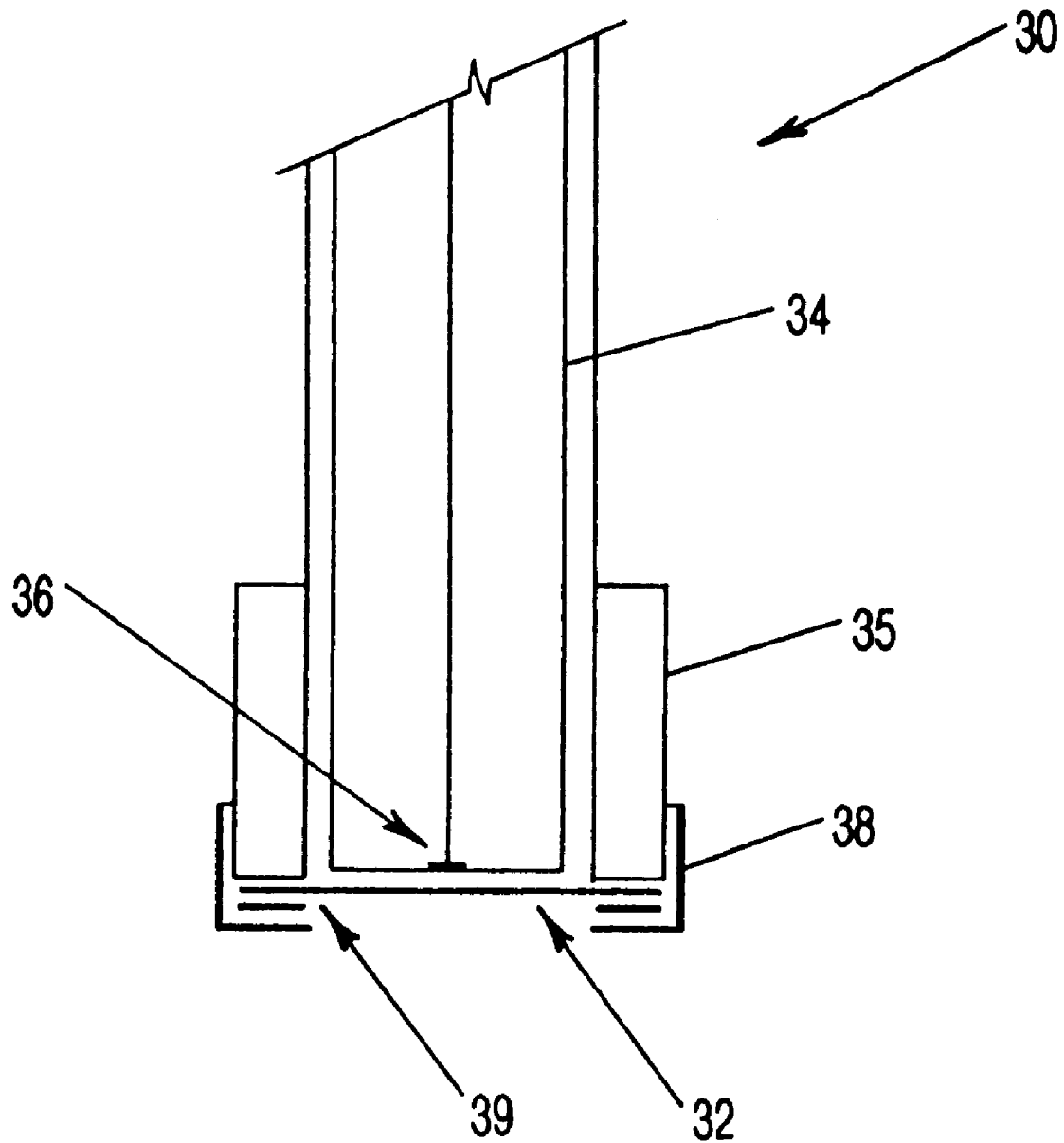
FIG. 10 shows a second probe embodiment.

FIG. 10 depicts another embodiment that is trace metal and organic pollutant probe 30 in which the membrane is held differently from the probe 10 of FIG. 1. Probe 30 comprises housing 35, further comprising grooves 34 for accommodating reagent inlet and outlet tubes. Gold working electrode 36 is positioned proximate the reagent flow. Screw-on cap 38 secures O-ring 39 against permeable membrane 32; membrane 32 permits sample (analyte) flow toward electrode 36, but excludes surfactants.

Again, as in the preferred embodiment, continuous reagent flow over the working electrode enhances monitoring, prevents surfactant contamination, greatly extends the linear range of measurements, and promotes ease of electrode cleaning. Similarly, detection of organic pollutant levels upon reaction with a suitable flowing reagent, is rendered possible. For example, the reagent may be an enzyme if the enzyme chosen is used as part of the reagent and the derivitization reaction to convert the analyte (an organic substrate) to a detectable species. Effective monitoring of several environmentally significant substrates can be accomplished by the enzymes listed in Table 1, which can be used as reagents for monitoring/detecting the appropriate target pollutant substrates as shown. Further, the reagent may be another biological molecule, such as an ssDNA-modified or a dsDNA-modified molecule, as long as it is included in the reagent solution.

TABLE 1

Enzymes and Target Substrates

| Enzyme | Substrate (Target Pollutants) |
|---|---|
| Nitrate reductase | Nitrate |
| Formaldehyde dehydrogenase | Formaldehyde |
| Horseradish peroxidase | Hydrogen peroxide, organic peroxide |
| Sulfite oxidase | Sulfite |
| Tyrosinase | Chlorophenols |
| Nitrilase | Organonitriles |
| Cholinesterase | Organophosphate Pesticides, Cyanide |

In addition to detection of organic or mixed waste, in-situ monitoring of various toxins inhibiting biocatalytic activity is possible with enzyme reagents. For example, inhibition of acetylcholinesterase can monitor organophosphate pesticides.

For other than natural water pH ranges, the probes of FIGS. 1 and 10 permit "optimal" pH delivery.

Another variation involves the use of electrodes for real-time monitoring of mutagens and carcinogens, either remotely or in laboratory applications. The association of various damaging agents with flowing ds-DNA reagent can be monitored via changes in the anodic response of the nucleic acid.

Such changes may result from chemical, structural or conformational variations of the nucleic acid probe.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. An electrochemical sensing apparatus comprising:
   an electrode;
   means for repeatedly introducing a reagent to an analyte said means for repeatedly introducing comprising a microdialysis sampling tube;
   means for continuously circulating the reagent; and
   means for electrochemically detecting a target sample.

2. The apparatus of claim 1 wherein said means for electrochemically detecting is selected from the group consisting of voltammetric detecting means, chronopotentiometric detecting means, and adsorptive stripping means.

3. The apparatus of claim 1 wherein said means for continuously circulating reagent comprises means for forming a target complex and adsorptively accumulating the complex in the absence of electrodepositing the target complex on said electrode and means for delivering the accumulated target complex to said means for electrochemically detecting.

4. The apparatus of claim 1 further comprising means for passivating surfactant contamination.

5. The apparatus of claim 4 wherein said means for passivating surfactant contamination comprises means for preventing surfactant permeation.

6. The apparatus of claim 1 further comprising means for cleaning the electrode.

7. The apparatus of claim 1 wherein said electrode is a working electrode selected from the group consisting of solid working electrodes, bare solid working electrodes, Hg-coated solid working electrodes, and glassy carbon Hg-coated electrodes.

8. The apparatus of claim 7 wherein said electrode is a solid working electrode selected from the group consisting of gold, carbon, platinum and iridium electrodes.

9. The apparatus of claim 1 wherein the reagent comprises a reagent selected from the group consisting of propyl gallate, dimethylglyoxime, enzymes, dsDNA, and ssDNA.

10. The apparatus of claim 1 wherein the analyte is selected from the group consisting of metal analytes and organic analytes.

11. The apparatus of claim 10 wherein the analyte comprises a metal selected from the group consisting of chromium, uranium, iron, aluminum, nickel and cobalt.

12. An electrochemical method of detecting metal and organic pollutants in analytes, comprising the steps of:
   a) providing an electrode;
   b) repeatedly introducing a reagent through a microdialysis sampling tube, to an analyte;
   c) continuously circulating the reagent; and
   d) electrochemically detecting a target sample.

13. The method of claim 12, wherein the step of providing an electrode comprises the step of providing electrodes selected from the group consisting of working electrodes, solid working electrodes, bare solid working electrode, Hg-coated solid working electrodes and glassy carbon Hg-coated electrodes.

14. The method of claim 13 wherein the step of providing an electrode comprises the step of providing a solid working electrode selected from the group consisting of carbon, gold, platinum and iridium electrodes.

15. The method of claim 12 wherein the step of continuously circulating a reagent comprises the step of circulating a reagent selected from the group consisting of propyl gallate, dimethylglyoxime, enzymes, dsDNA and ssDNA.

16. The method of claim 12 wherein the step of continuously a circulating reagent comprises the step of providing reagent delivery inlet and outlet tubes.

17. The method of claim 12 wherein the step of continuously circulating the reagent comprises forming a target complex and adsorptively accumulating the complex in the absence of electrodepositing the target complex on the electrode, and comprising the further step of delivering the accumulated target complex to a downstream detector.

18. The method of claim 12 wherein the step of electrochemically detecting comprises performing electrochemical measurement selected from the group consisting of voltammetric measurement, chronopotentiometric and adsorptive stripping measurement.

* * * * *